(12) United States Patent
Howard, Jr. et al.

(10) Patent No.: US 9,966,542 B2
(45) Date of Patent: May 8, 2018

(54) ELECTROACTIVE MATERIALS

(71) Applicant: E I DU PONT DE NEMOURS AND COMPANY, Wilmington, DE (US)

(72) Inventors: Michael Henry Howard, Jr., Montchanin, DE (US); Htay Min Hlaing, Wilmington, DE (US); Greg A Hostetler, Newark, DE (US); Denis Yurievich Kondakov, Wilmington, DE (US); Kerwin D Dobbs, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 43 days.

(21) Appl. No.: 15/171,482

(22) Filed: Jun. 2, 2016

(65) Prior Publication Data

US 2017/0352815 A1    Dec. 7, 2017

(51) Int. Cl.

| | | |
|---|---|---|
| *H01L 51/00* | (2006.01) | |
| *C09K 11/06* | (2006.01) | |
| *C09K 11/02* | (2006.01) | |
| *C07D 487/04* | (2006.01) | |
| *H01L 51/50* | (2006.01) | |

(52) U.S. Cl.
CPC ........ *H01L 51/0072* (2013.01); *C07D 487/04* (2013.01); *C09K 11/025* (2013.01); *C09K 11/06* (2013.01); *H01L 51/0067* (2013.01); *H01L 51/0085* (2013.01); *C09K 2211/1007* (2013.01); *C09K 2211/1029* (2013.01); *C09K 2211/185* (2013.01); *H01L 51/5012* (2013.01); *H01L 51/5072* (2013.01); *H01L 2251/5384* (2013.01)

(58) Field of Classification Search
CPC .............. H01L 51/0072; H01L 51/0067; H01L 51/0085; H01L 51/5012; H01L 51/5072; H01L 2251/5384; C09K 11/06; C09K 11/025; C09K 2211/1007; C09K 2211/1029; C09K 2211/185; C07D 487/04
USPC ........................................................ 428/690
See application file for complete search history.

(56) References Cited

U.S. PATENT DOCUMENTS

| | | |
|---|---|---|
| 6,670,645 B2 | 12/2003 | Grushin et al. |
| 6,875,524 B2 | 4/2005 | Hatwar et al. |
| 7,276,716 B1 | 10/2007 | Munro, III |
| 7,351,358 B2 | 4/2008 | Hsu et al. |
| 7,431,866 B2 | 10/2008 | Hsu et al. |
| 7,462,298 B2 | 12/2008 | Hsu et al. |
| 8,062,769 B2 | 11/2011 | Kai et al. |
| 8,968,883 B2 | 3/2015 | Rostovtsev et al. |
| 2004/0102577 A1 | 5/2004 | Hsu et al. |
| 2004/0127637 A1 | 7/2004 | Hsu et al. |
| 2005/0158577 A1 | 7/2005 | Ishibashi et al. |
| 2005/0184287 A1 | 8/2005 | Herron et al. |
| 2005/0205860 A1 | 9/2005 | Hsu et al. |
| 2007/0063638 A1 | 3/2007 | Tokairin et al. |
| 2007/0292713 A9 | 12/2007 | Dobbs et al. |
| 2009/0072727 A1 | 3/2009 | Takeda |
| 2013/0248849 A1* | 9/2013 | Feldman ................ C09K 11/06 257/40 |

FOREIGN PATENT DOCUMENTS

| | | |
|---|---|---|
| EP | 2080762 A1 | 7/2009 |
| WO | 2003/040257 A1 | 5/2003 |
| WO | 2003/063555 A1 | 7/2003 |
| WO | 2004/016710 A1 | 2/2004 |
| WO | 2005/052027 A1 | 6/2005 |
| WO | 2007/021117 A1 | 2/2007 |
| WO | 2007/145979 A3 | 4/2008 |
| WO | 2009/018009 A1 | 2/2009 |
| WO | 2012/087955 A1 | 6/2012 |
| WO | 2013/142634 A1 | 9/2013 |
| WO | 2016/017684 A1 | 2/2016 |
| WO | WO 2016017684 A1 * | 2/2016 ............. C09K 11/06 |

OTHER PUBLICATIONS

Bogdanowicz et al. "The Synthesis and Antibacterial Activity of Novel 4-Pyrrolidin-3-cyanopyridine Derivatives", Journal of Heterocyclic Chemistry, 2013, vol. 50, Issue 3, pp. 544-550.*
Wang_PhotoconductiveMaterials_Kirk Othmer Encyclopedia of Chemical Technology, Fourth Edition_1996_vol. 18_pp. 837-860.
Robertson_PreparationXRayStructure_JMaterChem_2000_pp. 2043-2047.
Pindur_Indolo32bCarbazolReaktionsprodukt_ArchPharm_1987_pp. 280-282.
Knolker_IronMediatedSynthesis_TetraLett_1998_pp. 4007-4008.
Janosik_Reactionsof23biindolyl_Tetrahedron_1999_pp.  2371-2380.

(Continued)

*Primary Examiner* — Michael M Bernshteyn

(57) ABSTRACT

There is disclosed a compound which is an N-heterocycle having at least one substituent of Formula 1:

(I)

$$\begin{array}{c}*\\|\\Q1{=}\!\!\!\!\!\diagdown\!\!\!\!\!\!\!\!Q5\\||\phantom{xxx}|\\Q2\!\!\!\!\diagdown\!\!\!\!\!\!\!\!\!\diagup Q4\\Q3\end{array}$$

wherein: the N-heterocycle is a fused ring N-heterocycle having at least two fused aromatic rings with at least one ring N; Q1, Q2, Q4, and Q5 are the same or different and are selected from the group consisting of N and $CR^1$; Q3 is C—CN; $R^1$ is the same or different at each occurrence and is selected from the group consisting of H, D, CN, hydrocarbon aryl, heteroaryl, deuterated hydrocarbon aryl, and deuterated heteroaryl; and * represents a point of attachment to N in the N-heterocycle; with the proviso that at least one of Q1, Q2, Q4, and Q5 is N.

17 Claims, 2 Drawing Sheets

(56) References Cited

OTHER PUBLICATIONS

Gustafsson_FlexibleLightEmittingDiodes_Nature_Jun. 11, 1992_vol. 357_pp. 477-479.
Desarbre_SynthesisSymmetricNonSymmetric_JChemSoc_1998_pp. 2009-2016.
CRC Handbook of Chemistry and Physics, 81st Edition (2000-2001)_Book_Not_Included.
Li et al,"A Significantly Twisted Spirocyclic Phosphine Oxide as a Universal Host for High-Efficiency Full-Color Thermally Activated Delayed Fluorescence Diodes", Advanced Materials, 2016, vol. 28(16), pp. 3122-3130.
International Search Report, PCT/US17/34434, Kam Yoo Lim, Authorized Officer, KIP, Sep. 6, 2017.
Bogdanowicz et al, "The Synthesis and Antibacterial Activity of Novel 4-Pyrrolidin-3-cyanopyridine Derivatives", Journal of Heterocyclic Chemistry 2013, vol. 50(3), pp. 544-550.

\* cited by examiner

ELECTROACTIVE MATERIALS

BACKGROUND INFORMATION

Field of the Disclosure

The present disclosure relates to novel electroactive compounds. The disclosure further relates to electronic devices having at least one layer comprising such an electroactive compound.

Description of the Related Art

In organic electronic devices, such as organic light emitting diodes ("OLED"), that make up OLED displays, one or more organic electroactive layers are sandwiched between two electrical contact layers. In an OLED at least one organic electroactive layer emits light through the light-transmitting electrical contact layer upon application of a voltage across the electrical contact layers.

It is well known to use organic electroluminescent compounds as the light-emitting component in light-emitting diodes. Simple organic molecules, conjugated polymers, and organometallic complexes have been used. The light-emitting materials may be used alone or may be present in an electroactive host material.

Devices that use electroluminescent materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for electroactive materials for use in electronic devices.

SUMMARY

There is disclosed a compound which is an N-heterocycle having at least one substituent of Formula 1:

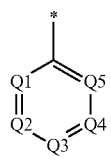

(I)

wherein: the N-heterocycle is a fused ring N-heterocycle having at least two fused aromatic rings with at least one ring N; Q1, Q2, Q4, and Q5 are the same or different and are selected from the group consisting of N and $CR^1$; Q3 is C—CN; $R^1$ is the same or different at each occurrence and is selected from the group consisting of H, D, CN, hydrocarbon aryl, heteroaryl, deuterated hydrocarbon aryl, and deuterated heteroaryl; and * represents a point of attachment to N in the N-heterocycle; with the proviso that at least one of Q1, Q2, Q4, and Q5 is N.

There is also provided a composition comprising (a) a dopant capable of electroluminescence having an emission maximum between 380 and 750 nm, (b) a first host compound comprising an N-heterocycle having a substituent of Formula I, and (c) a second host compound.

There is also provided an electronic device having at least one layer comprising a compound comprising an N-heterocycle having a substituent of Formula I.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
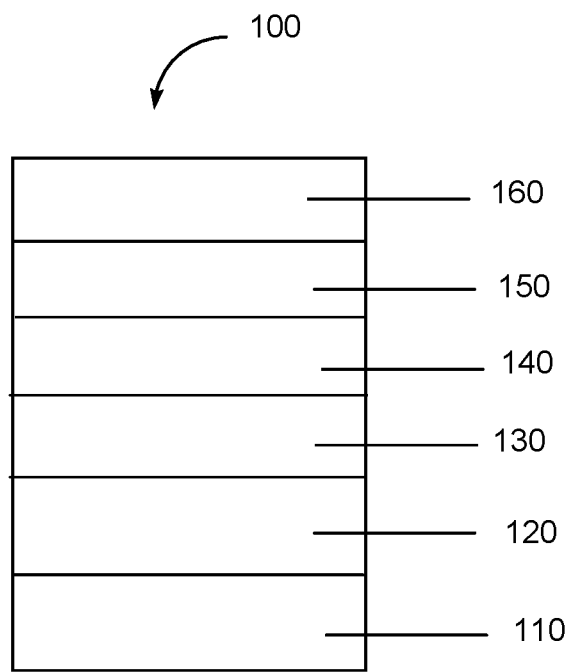
FIG. 1 includes an illustration of one example of an organic electronic device including the new compound described herein.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a compound which is an N-heterocycle having at least one substituent of Formula I, as described in detail below.

There is further provided a composition comprising (a) a dopant capable of electroluminescence having an emission maximum between 380 and 750 nm, (b) a first host compound which is an N-heterocycle having at least one substituent of Formula I, and (c) a second host compound.

There is further provided an electronic device having at least one layer comprising a compound which is an N-heterocycle having at least one substituent of Formula I.

There is further provided an electronic device having at least one layer comprising one of the compositions described above.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compound Having a Substituent of Formula I, the Composition Including a Compound Having a Substituent of Formula I, the Electronic Device, and finally Examples.

1. Definitions and Clarification of Terms

Before addressing details of embodiments described below, some terms are defined or clarified.

As used in the "Definitions and Clarification of Terms", R, R' and R" and any other variables are generic designations and may be the same as or different from those defined in the formulas.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aromatic compound" is intended to mean an organic compound comprising at least one unsaturated cyclic group having 4n+2 delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like.

The term "aryl" or "aryl group" means a moiety derived from an aromatic compound. A group "derived from" a compound, indicates the radical formed by removal of one or more hydrogen ("H") or deuterium ("D"). The aryl group may be a single ring (monocyclic) or have multiple rings (bicyclic, or more) fused together or linked covalently. A "hydrocarbon aryl" has only carbon atoms in the aromatic ring(s). A "heteroaryl" has one or more heteroatoms in at least one aromatic ring. In some embodiments, hydrocarbon aryl groups have 6 to 60 ring carbon atoms; in some embodiments, 6 to 30 ring carbon atoms. In some embodiments, heteroaryl groups have from 4-50 ring carbon atoms; in some embodiments, 4-30 ring carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include D, alkyl, aryl, nitro, cyano, —N(R')(R"), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxy, siloxane, thioalkoxy, —S(O)$_2$—, —C(=O)—N(R')(R"), (R')(R")N-alkyl, (R')(R")N-alkoxyalkyl, (R')(R")N-alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups. Any of the preceding groups with available hydrogens, may also be deuterated.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" as it refers to a layer or a material, is intended to indicate a layer or material which electronically facilitates the operation of the device. Examples of electroactive materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group have been replaced with fluorine.

The term "germyl" refers to the group $R_3Ge$—, where R is the same or different at each occurrence and is H, D, C1-20 alkyl, deuterated alkyl, fluoroalkyl, aryl, or deuterated aryl. A deuterated germyl group is one in which one or more R groups are deuterated.

The prefix "hetero" indicates that one or more carbon atoms have been replaced with a different atom. In some embodiments, the heteroatom is O, N, S, or combinations thereof.

The term "host material" is intended to mean a material to which a dopant is added. The host material may or may not have electronic characteristic(s) or the ability to emit, receive, or filter radiation. In some embodiments, the host material is present in higher concentration.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "photoactive" refers to a material or layer that emits light when activated by an applied voltage (such as in a light emitting diode or chemical cell), that emits light after the absorption of photons (such as in down-converting phosphor devices), or that responds to radiant energy and generates a signal with or without an applied bias voltage (such as in a photodetector or a photovoltaic cell).

The term "siloxane" refers to the group $R_3SiOR_2Si$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si. A deuterated siloxane group is one in which one or more R groups are deuterated.

The term "siloxy" refers to the group $R_3SiO$—, where R is the same or different at each occurrence and is H, D, C1-20 alkyl, deuterated alkyl, fluoroalkyl, aryl, or deuterated aryl. A deuterated siloxy group is one in which one or more R groups are deuterated.

The term "silyl" refers to the group $R_3Si-$, where R is the same or different at each occurrence and is H, D, C1-20 alkyl, deuterated alkyl, fluoroalkyl, aryl, or deuterated aryl. In some embodiments, one or more carbons in an R alkyl group are replaced with Si. A deuterated silyl group is one in which one or more R groups are deuterated.

In a structure where a substituent bond passes through one or more rings as shown below,

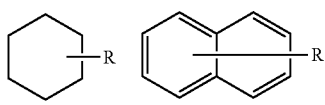

it is meant that the substituent R may be bonded at any available position on the one or more rings.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). Exemplary adjacent R groups are shown below:

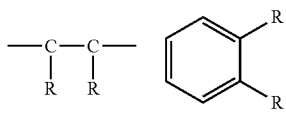

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81st Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Compound Having a Substituent of Formula I

A compound is provided, wherein the compound is an N-heterocycle having a substituent of Formula I

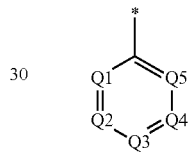

(I)

wherein:
Q1, Q2, Q3, Q4, and Q5 are the same or different and are selected from the group consisting of N and $CR^1$;
$R^1$ is the same or different at each occurrence and is selected from the group consisting of H, D, CN, hydrocarbon aryl, heteroaryl, deuterated hydrocarbon aryl, and deuterated heteroaryl; and
* represents a point of attachment to N in the N-heterocycle;
with the proviso that at least one of Q1 through Q5 is N and at least one of Q1 through Q5 is C—CN.

In some embodiments, the compound is deuterated. In some embodiments, the compound is at least 10% deuterated. By "% deuterated" or "% deuteration" is meant the ratio of deuterons to the sum of protons plus deuterons, expressed as a percentage. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments, deuteration is present on the N-heterocycle.

In some embodiments, deuteration is present on the substituent of Formula I.

In some embodiments, deuteration is present on both the N-heterocycle and the substituent of Formula I.

In some embodiments, the N-heterocycle is a fused ring N-heterocycle having at least two fused aromatic rings with at least one ring N. In some embodiments, the N-heterocycle has at least three fused aromatic rings with at least one ring N.

In some embodiments, the N-heterocycle is selected from the group consisting of carbazole, benzocarbazole, dibenzocarbazole, indolocarbazole, indole, indoloindole, substituted derivatives thereof, and deuterated analogs thereof.

In some embodiments, the N-heterocycle is selected from the group consisting of benzocarbazole, dibenzocarbazole, indolocarbazole, indole, indoloindole, substituted derivatives thereof, and deuterated analogs thereof.

In some embodiments, the N-heterocycle is selected from the group consisting of indolocarbazole, indole, indoloindole, substituted derivatives thereof, and deuterated analogs thereof.

In some embodiments, the N-heterocycle is a carbazole having Formula II

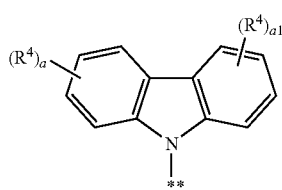

(II)

wherein:
R$^4$ is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent R$^4$ groups can be joined together to form a fused ring;

a and a1 are the same or different and are an integer from 0 to 4; and

** represents a point of attachment to the substituent having Formula I.

In some embodiments of Formula II, a=0.
In some embodiments of Formula II, a=1.
In some embodiments of Formula II, a=2.
In some embodiments of Formula II, a=3.
In some embodiments of Formula II, a=4.
In some embodiments of Formula II, a>0.
In some embodiments of Formula II, a>0 and at least one R$^4$ is D.
In some embodiments of Formula II, a>0 and at least one R$^4$ is alkyl or deuterated alkyl. In some embodiments, the alkyl has 1-20 carbons; in some embodiments, 1-12 carbons; in some embodiments, 1-8 carbons.
In some embodiments of Formula II, a>0 and at least one R$^4$ is hydrocarbon aryl or deuterated hydrocarbon aryl.
In some embodiments of Formula II, a>0 and at least one R$^4$ has Formula a

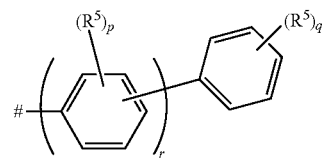

Formula a where:
R$^5$ is the same or different at each occurrence and is selected from the group consisting of D, alkyl, alkoxy, siloxane, silyl, germyl, diarylamino, carbazolyl, deuterated alkyl, deuterated alkoxy, deuterated siloxane, deuterated silyl, deuterated germyl, deuterated diarylamino, and deuterated carbazolyl, where adjacent R$^5$ groups can be joined together to form an fused aromatic ring or a deuterated fused aromatic ring;
p is the same or different at each occurrence and is an integer from 0-4;
q is an integer from 0-5;
r is an integer from 1 to 5; and
# indicates a point of attachment.

In some embodiments of Formula II, a>0 and at least one R$^4$ has Formula b

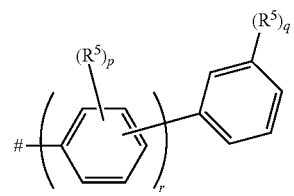

Formula b where R$^5$, p, q, r and # are as in Formula a.

In some embodiments of Formula II, a>0 and at least one R$^4$ is selected from the group consisting of phenyl, naphthyl, biphenyl, substituted derivatives thereof, and deuterated analogs thereof. In some embodiments, the substituents are selected from the group consisting of D, alkyl, alkoxy, silyl, germyl, deuterated alkyl, deuterated alkoxy, deuterated silyl, deuterated germyl, and combinations thereof.

In some embodiments of Formula II, a1=0.
In some embodiments of Formula II, a1=1.
In some embodiments of Formula II, a1=2.
In some embodiments of Formula II, a1=3.
In some embodiments of Formula II, a1=4.
In some embodiments of Formula II, a1>0.
In some embodiments of Formula II, a1>0 and at least one R$^4$ is as described above.

In some embodiments, the N-heterocycle is a benzocarbazole having Formula II-a, Formula II-b, or Formula II-c

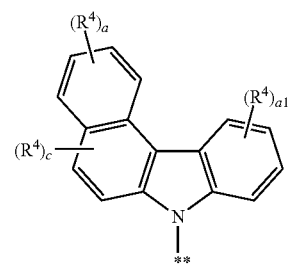

(II-a)

-continued

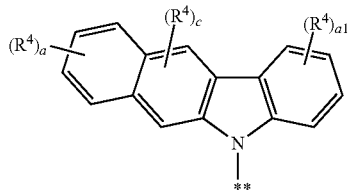
(II-b)

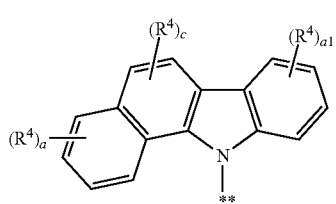
(II-c)

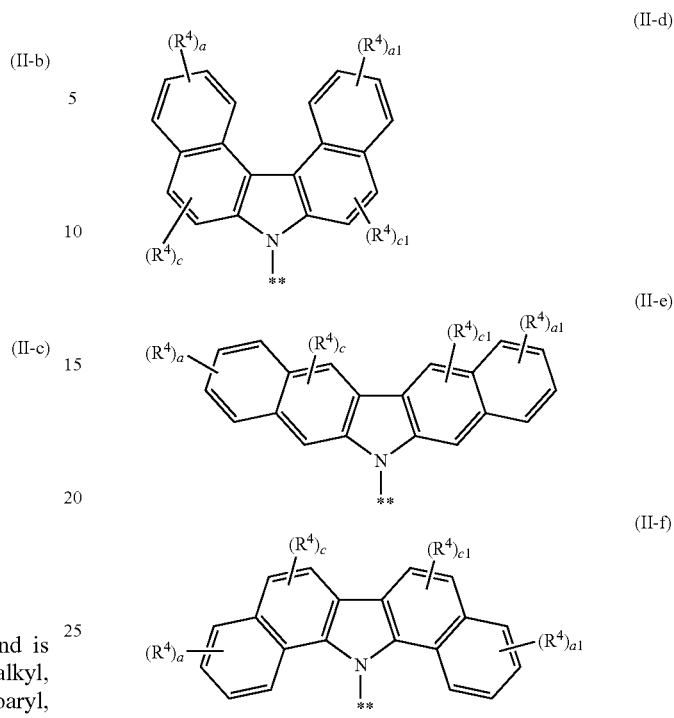

wherein:

$R^4$ is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent $R^4$ groups can be joined together to form a fused ring;

a and a1 are the same or different at each occurrence and are an integer from 0-4;

c is the same or different at each occurrence and is an integer from 0-2; and

** represents a point of attachment to the substituent having Formula I.

In some embodiments, the N-heterocycle has Formula II-a.

In some embodiments, the N-heterocycle has Formula II-b.

In some embodiments, the N-heterocycle has Formula II-c.

In some embodiments of Formula II-a, Formula II-b, and Formula II-c, c=0.

In some embodiments of Formula II-a, Formula II-b, and Formula II-c, c=1.

In some embodiments of Formula II-a, Formula II-b, and Formula II-c, c=2.

In some embodiments of Formula II-a, Formula II-b, and Formula II-c, c>0.

The above-described embodiments for a, a1, and $R^4$ in Formula II, apply equally to a, a1, and $R^4$ in Formula II-a, Formula II-b, and Formula II-c.

In some embodiments, the N-heterocycle is a dibenzocarbazole having Formula II-d, Formula II-e, or Formula II-f wherein:

$R^4$ is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent $R^4$ groups can be joined together to form a fused ring;

a and a1 are the same or different at each occurrence and are an integer from 0-4;

c and c1 are the same or different at each occurrence and are an integer from 0-2; and

** represents a point of attachment to the substituent having Formula I.

In some embodiments, the N-heterocycle has Formula II-d.

In some embodiments, the N-heterocycle has Formula II-e.

In some embodiments, the N-heterocycle has Formula II-f.

In some embodiments of Formula II-d, Formula II-e, and Formula II-f, c1=0.

In some embodiments of Formula II-d, Formula II-e, and Formula II-f, c1=1.

In some embodiments of Formula II-d, Formula II-e, and Formula II-f, c1=2.

In some embodiments of Formula II-d, Formula II-e, and Formula II-f, c1>0.

The above-described embodiments for a, a1, c, and $R^4$ in Formula II-a, apply equally to a, a1, c, and $R^4$ in Formula II-d, Formula II-e, and Formula II-f.

In some embodiments, the N-heterocycle is an indole having Formula III-a

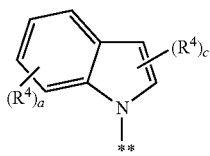
(III-a)

wherein:
- R[4] is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent R[4] groups can be joined together to form a fused ring;
- a is an integer from 0-4;
- c is an integer from 0-2; and
- ** represents a point of attachment to the substituent having Formula I.

The above-described embodiments for a, c, and R[4] in Formula II-a, apply equally to a, c, and R[4] in Formula III-a.

In some embodiments, the N-heterocycle is an indoloindole having Formula III-b

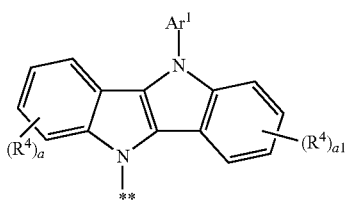
(III-b)

wherein:
- Ar[1] is selected from the group consisting of hydrocarbon aryl, heteroaryl, and deuterated analogs thereof;
- R[4] is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent R[4] groups can be joined together to form a fused ring;
- a and a1 are the same or different and are an integer from 0-4; and
- ** represents a point of attachment to the substituent having Formula I.

In some embodiments of Formula III-b, Ar[1] is a hydrocarbon aryl or deuterated analog thereof. In some embodiments, the hydrocarbon aryl has 6-24 ring carbons.

In some embodiments of Formula III-b, Ar[1] has Formula a, as defined above.

In some embodiments of Formula III-b, Ar[1] has Formula b, as defined above.

In some embodiments of Formula III-b, Ar[1] is a hydrocarbon aryl having no non-aromatic substituents.

In some embodiments of Formula III-b, Ar[1] is a deuterated hydrocarbon aryl having no other substituents.

In some embodiments of Formula III-b, Ar[1] is a substituted hydrocarbon aryl. In some embodiments, the substituents are selected from the group consisting of D, alkyl, alkoxy, silyl, germyl, deuterated alkyl, deuterated alkoxy, deuterated silyl, deuterated germyl, and combinations thereof.

In some embodiments of Formula III-b, Ar[1] is selected from the group consisting of phenyl, naphthyl, biphenyl, binaphthyl, terphenyl, substituted derivatives thereof, and deuterated analogs thereof.

The above-described embodiments for a, a1, and R[4] in Formula II-a, apply equally to a, a1, and R[4] in Formula III-b.

In some embodiments, the N-heterocycle is an indolocarbazole having Formula IV-a, Formula IV-b, Formula IV-c, Formula IV-d, or Formula IV-e

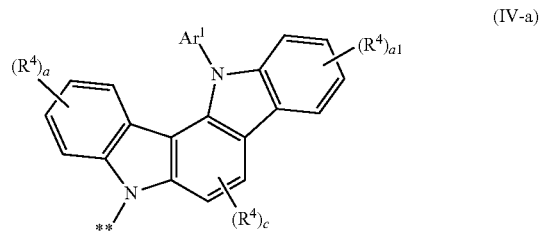
(IV-a)

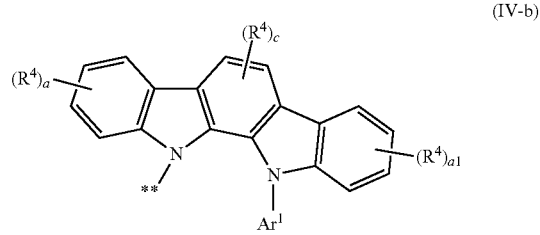
(IV-b)

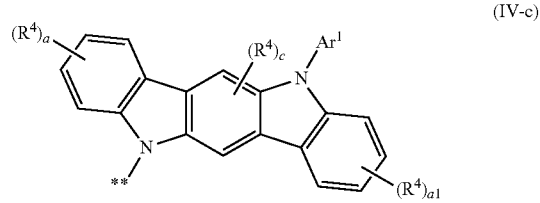
(IV-c)

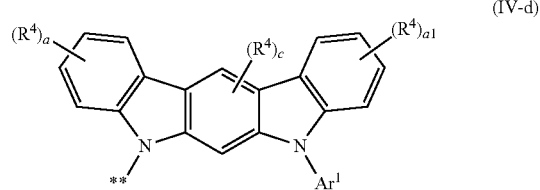
(IV-d)

-continued

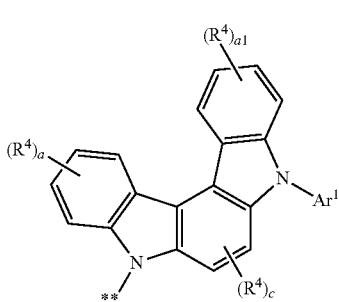

(IV-e)

wherein:
Ar¹ is selected from the group consisting of hydrocarbon aryl, heteroaryl, and deuterated analogs thereof;
R⁴ is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent R⁴ groups can be joined together to form a fused ring;
a and a1 are the same or different at each occurrence and are an integer from 0-4;
c is an integer from 0-2; and
** represents a point of attachment to the substituent having Formula I.

In some embodiments, the N-heterocycle has Formula IV-a.

In some embodiments, the N-heterocycle has Formula IV-b.

In some embodiments, the N-heterocycle has Formula IV-c.

In some embodiments, the N-heterocycle has Formula IV-d.

In some embodiments, the N-heterocycle has Formula IV-e.

The above-described embodiments for a, a1, c, Ar¹, and R⁴ in Formula III-b, apply equally to a, a1, c, Ar¹, and R⁴ in Formula IV-a, Formula IV-b, Formula IV-c, Formula IV-d, and Formula IV-e.

The N-heterocycle has at least one substituent having Formula I

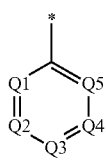

(I)

wherein:
Q1, Q2, Q3, Q4, and Q5 are the same or different and are selected from the group consisting of N and CR¹;
R¹ is the same or different at each occurrence and is selected from the group consisting of H, D, CN, hydrocarbon aryl, heteroaryl, deuterated hydrocarbon aryl, and deuterated heteroaryl; and

* represents a point of attachment to N in the N-heterocycle;
with the proviso that at least one of Q1 through Q5 is N and at least one of Q1 through Q5 is C—CN.

The substituent of Formula I is attached directly to a ring nitrogen in the N-heterocycle.

In some embodiments, the N-heterocycle has a single substituent of Formula I.

In some embodiments of Formula I, Q1=N.
In some embodiments of Formula I, Q2=N.
In some embodiments of Formula I, Q3=N.
In some embodiments of Formula I, Q4=N.
In some embodiments of Formula I, Q5=N.
In some embodiments of Formula I, Q1=CR¹.
In some embodiments of Formula I, Q2=CR¹.
In some embodiments of Formula I, Q3=CR¹.
In some embodiments of Formula I, Q4=CR¹.
In some embodiments of Formula I, Q5=CR¹.
In some embodiments of Formula I, Q1=C—CN.
In some embodiments of Formula I, Q2=C—CN.
In some embodiments of Formula I, Q3=C—CN.
In some embodiments of Formula I, Q4=C—CN.
In some embodiments of Formula I, Q5=C—CN.
In some embodiments of Formula I, two of Q1 through Q5 are N.

In some embodiments of Formula I, only one of Q1 through Q5 is C—CN.

In some embodiments of Formula I, at least one of Q1 through Q5 is CR¹ where R¹ is H or D.

In some embodiments of Formula I, at least one of Q1 through Q5 is CR¹ where R¹ is a hydrocarbon aryl or deuterated analog thereof. In some embodiments, the hydrocarbon aryl has 6-24 ring carbons.

In some embodiments of Formula I, at least one of Q1 through Q5 is CR¹ where R¹ has Formula a, as defined above.

In some embodiments of Formula I, at least one of Q1 through Q5 is CR¹ where R¹ has Formula b, as defined above.

In some embodiments of Formula I, at least one of Q1 through Q5 is CR¹ where R¹ is a hydrocarbon aryl having no non-aromatic substituents.

In some embodiments of Formula I, at least one of Q1 through Q5 is CR¹ where R¹ is a deuterated hydrocarbon aryl having no other substituents.

In some embodiments of Formula I, at least one of Q1 through Q5 is CR¹ where R¹ is a substituted hydrocarbon aryl. In some embodiments, the substituents are selected from the group consisting of D, alkyl, alkoxy, silyl, germyl, deuterated alkyl, deuterated alkoxy, deuterated silyl, deuterated germyl, and combinations thereof.

In some embodiments of Formula I, at least one of Q1 through Q5 is CR¹ where R¹ is selected from the group consisting of phenyl, naphthyl, biphenyl, binaphthyl, terphenyl, substituted derivatives thereof, and deuterated analogs thereof.

In some embodiments of Formula I, at least one of Q1 through Q5 is CR¹ where R¹ is an aryloxy or deuterated aryloxy group.

In some embodiments of Formula I, at least one of Q1 through Q5 is CR¹ where R¹ is a hydrocarbon aryloxy or deuterated hydrocarbon aryloxy group. In some embodiments, the aryl part of the aryloxy group has 6-18 ring carbons; in some embodiments, 6-12 ring carbons.

In some embodiments of Formula I, at least one of Q1 through Q5 is CR¹ where R¹ is selected from the group consisting of phenoxy, substituted derivatives thereof, and deuterated analogs thereof.

In some embodiments, the substituent on the N-heterocycle has Formula IA

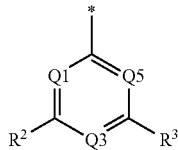

(IA)

wherein:
Q1, Q3, and Q5 are the same or different and are selected from the group consisting of N and CR¹;
R¹, R², and R³ are the same or different at each occurrence and are selected from the group consisting of H, D, CN, hydrocarbon aryl, heteroaryl, deuterated hydrocarbon aryl, and deuterated heteroaryl; and
* represents a point of attachment to N in the N-heterocycle;
with the proviso that at least one of Q1, Q3, and Q5 is N and at least one of Q1, Q3, and Q5 is C—CN.

In some embodiments of Formula IA, Q1=N.
In some embodiments of Formula IA, Q3=N.
In some embodiments of Formula IA, Q5=N.
In some embodiments of Formula IA, Q1=CR³.
In some embodiments of Formula IA, Q3=CR³.
In some embodiments of Formula IA, Q5=CR³.
In some embodiments of Formula IA, Q1=C—CN.
In some embodiments of Formula IA, Q3=C—CN.
In some embodiments of Formula IA, Q5=C—CN.
In some embodiments of Formula IA, R²=R³.
In some embodiments of Formula IA, R²≠R³.
In some embodiments of Formula IA, R² is H or D.
In some embodiments of Formula IA, R² is a hydrocarbon aryl or deuterated analog thereof. In some embodiments, the hydrocarbon aryl has 6-24 ring carbons.
In some embodiments of Formula IA, R² has Formula a, as defined above.
In some embodiments of Formula IA, R² has Formula b, as defined above.
In some embodiments of Formula IA, R² is a hydrocarbon aryl having no non-aromatic substituents.
In some embodiments of Formula IA, R² is a deuterated hydrocarbon aryl having no other substituents.
In some embodiments of Formula IA, R² is a substituted hydrocarbon aryl. In some embodiments, the substituents are selected from the group consisting of D, alkyl, alkoxy, silyl, germyl, deuterated alkyl, deuterated alkoxy, deuterated silyl, deuterated germyl, and combinations thereof.
In some embodiments of Formula IA, R² is selected from the group consisting of phenyl, naphthyl, biphenyl, binaphthyl, terphenyl, substituted derivatives thereof, and deuterated analogs thereof.
In some embodiments of Formula IA, R² is an aryloxy or deuterated aryloxy group.
In some embodiments of Formula IA, R² is a hydrocarbon aryloxy or deuterated hydrocarbon aryloxy group. In some embodiments, the aryl part of the aryloxy group has 6-18 ring carbons; in some embodiments, 6-12 ring carbons.

In some embodiments of Formula IA, R² is selected from the group consisting of phenoxy, substituted derivatives thereof, and deuterated analogs thereof.

All of the above-described embodiments for R² apply equally to R³.

In some embodiments, the substituent has Formula IB

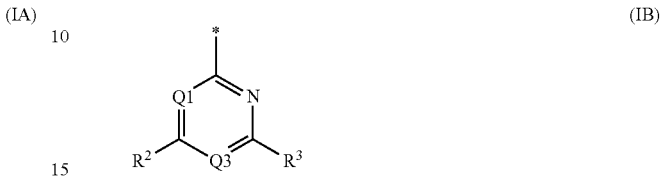

(IB)

wherein:
Q1 and Q3 are the same or different and are selected from the group consisting of N and CR¹;
R¹, R², and R³ are the same or different at each occurrence and are selected from the group consisting of H, D, CN, hydrocarbon aryl, heteroaryl, deuterated hydrocarbon aryl, and deuterated heteroaryl; and
* represents a point of attachment to N in the N-heterocycle;
with the proviso that at least one of Q1 and Q3 is C—CN.

In some embodiments of Formula IB, Q1=C—CN.
In some embodiments of Formula IB, Q3=C—CN.
In some embodiments of Formula IB, Q1=CR¹.
In some embodiments of Formula IB, Q3=CR¹.

All of the above-described embodiments for R¹, R², and R³ in Formula IA apply equally to R¹, R², and R³ in Formula IB.

Any of the above embodiments for the N-heterocycle and for the substituent group can be combined with one or more of the other embodiments, so long as they are not mutually exclusive. For example, the embodiment in which the N-heterocycle is a carbazole having Formula II can be combined with the embodiment in which the substituent has Formula IIA and combined with the embodiment in which Q1 is N and combined with the embodiment in which R²=R³ and is phenyl. The same is true for the other non-mutually-exclusive embodiments discussed above. The skilled person would understand which embodiments were mutually exclusive and would thus readily be able to determine the combinations of embodiments that are contemplated by the present application.

The compounds described herein can be made using any technique that will yield a C—C or C—N bond. A variety of such techniques are known, such as Suzuki, Yamamoto, Stille, and metal-catalyzed C—N couplings as well as metal catalyzed and oxidative direct arylation.

The core indolocarbazole of Formula IV-a can be synthesized according to a literature procedure from 2,3'-biindolyl: Janosik, T.; Bergman, J. Tetrahedron (1999), 55, 2371. 2,3'-biindolyl was synthesized according to the procedure described in Robertson, N.; Parsons, S.; MacLean, E. J.; Coxall, R. A.; Mount, Andrew R. Journal of Materials Chemistry (2000), 10, 2043.

The core indolocarbazole of Formula IV-b can be synthesized according to the procedure found in EP2080762A1 and U.S. Pat. No. 8,062,769.

The core indolocarbazole of Formula IV-c can be synthesized from commercially available 3,3'-methylenediindole according to the procedure found in: Pindur, U.; Müller, J. Arch. Pharm. (1987), 320, 280.

The core indolocarbazole of Formula IV-d can be synthesized according to the procedure found in Knolker, Hans-Joachim; Reddy, Kethiri R. Tetrahedron Letters (1998), 39(23), 4007-4008.

The core indolocarbazole of Formula IV-e can be synthesized according to the procedure found in Desarbre, Eric and Bergman, January; Journal of the Chemical Society, Perkin Transactions 1: Organic and Bio-Organic Chemistry, (13), 2009-2016; 1998

Deuterated compounds can be prepared in a similar manner using deuterated precursor materials or, more generally, by treating the non-deuterated compound with deuterated solvent, such as benzene-d6, in the presence of a Lewis acid H/D exchange catalyst, such as trifluoromethanesulfonic acid, aluminum trichloride or ethyl aluminum dichloride.

Exemplary preparations are given in the Examples.

Some non-limiting examples of N-heterocycle compounds having a substituent of Formula I are shown below.

Compound I-1

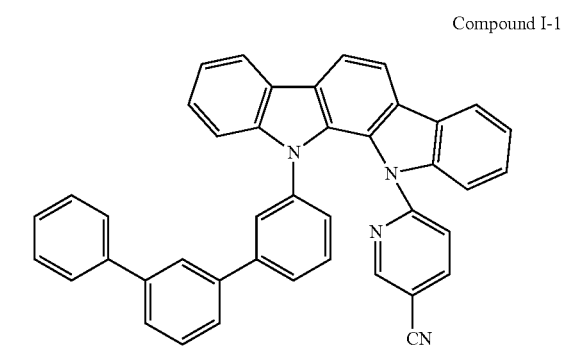

Compound I-2

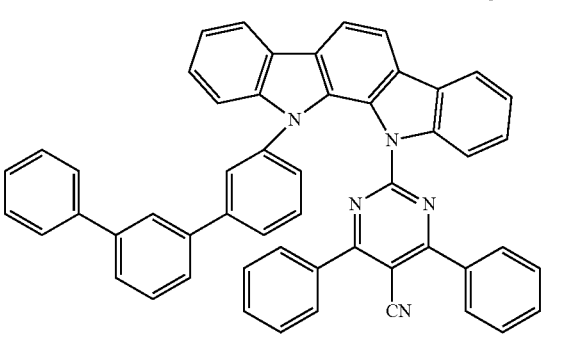

Compound I-3

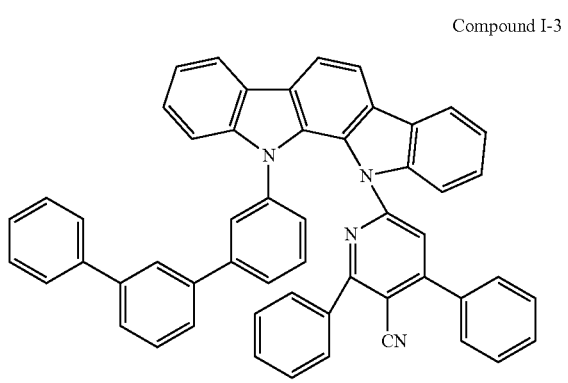

Compound I-4

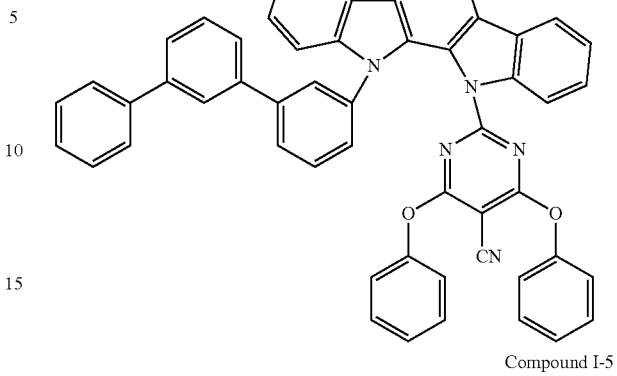

Compound I-5

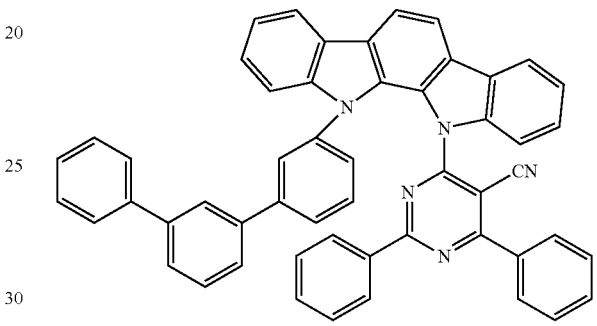

The N-heterocycle compounds having a substituent of Formula I can be formed into layers for electronic devices. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous liquid deposition techniques, include but are not limited to, spin coating, gravure coating, curtain coating, dip coating, slot-die coating, spray coating, and continuous nozzle coating. Discontinuous liquid deposition techniques include, but are not limited to, ink jet printing, gravure printing, and screen printing.

In some embodiments, the new N-heterocycle compounds having a substituent of Formula I can be used as hosts for electroluminescent materials in devices.

In some embodiments, the new N-heterocycle compounds having a substituent of Formula I can be used as electron transport materials in devices.

3. Composition Including an N-Heterocycle Having at Least One Substituent of Formula I In some embodiments, a composition is provided, where the composition comprises (a) a dopant capable of electroluminescence having an emission maximum between 380 and 750 nm, (b) a first host compound which is an N-heterocycle having at least one substituent of Formula I, and (c) a second host compound.

(a) Dopant

Electroluminescent ("EL") materials which can be used as a dopant in the photoactive layer, include, but are not limited to, small molecule organic luminescent compounds, luminescent metal complexes, conjugated polymers, and mixtures thereof. Examples of small molecule luminescent organic compounds include, but are not limited to, chrysenes, pyrenes, perylenes, rubrenes, coumarins, anthracenes, thiadiazoles, benzofluorenes, derivatives thereof, and mixtures thereof. Examples of metal complexes include, but are not limited to, metal chelated oxinoid compounds and cyclometallated complexes of metals such as iridium, rhodium, ruthenium, osmium, and platinum. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In some embodiments, the dopant is an organometallic complex. In some embodiments, the organometallic complex is cyclometallated. By "cyclometallated" it is meant that the complex contains at least one ligand which bonds to the metal in at least two points, forming at least one 5- or 6-membered ring with at least one carbon-metal bond. In some embodiments, the metal is iridium or platinum. In some embodiments, the organometallic complex is electrically neutral. Such materials have been disclosed in, for example, U.S. Pat. No. 6,670,645 and Published PCT Applications WO 03/063555, WO 2004/016710, and WO 03/040257.

In some embodiments, the dopant is a complex having the formula $$Ir(L1)_x(L2)_y(L3)_z;$$ where L1 is a monoanionic bidentate cyclometalating ligand coordinated through carbon and nitrogen;
L2 is a monoanionic bidentate ligand which is not coordinated through a carbon;
L3 is a monodentate ligand;
x is 1-3;
y and z are independently 0-2; and
x, y, and z are selected such that the iridium is hexacoordinate and the complex is electrically neutral.

Some examples of formulae include, but are not limited to, $Ir(L1)_3$; $Ir(L1)_2$ (L2); and $Ir(L1)_2$ (L3)(L3'), where L3 is anionic and L3' is nonionic. The ligands may be unsubstituted or substituted with F, D, alkyl, perfluororalkyl, alkoxyl, alkylamino, arylamino, CN, silyl, fluoroalkoxyl, aryl groups, or deuterated analogs thereof.

In some embodiments of the complex $Ir(L1)_3$, all three L1 ligands are the same and the complex is homoleptic.

In some embodiments of the complex $Ir(L1)_3$, at least one L1 ligand is different from the others and the complex is heteroleptic. In some embodiments, the heteroleptic complex has three different L1 ligands.

In some embodiments, L1 is an aryl N-heterocycle, where the aryl is phenyl or napthyl, and the N-heterocycle is pyridine, quinoline, isoquinoline, diazine, pyrrole, pyrazole or imidazole.

In some embodiments, L1 is selected from the group consisting of phenylpyridines, phenylquinolines, phenylisoquinolines, phenylpyrimidines, phenylpyrazoles, thienylpyridines, thienylquinolines, and thienylpyrimidines.

Monoanionic bidentate ligands, L2, are well known in the art of metal coordination chemistry. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanols (phosphinoalkoxide ligands).

In some embodiments, L2 is selected from the group consisting of β-dienolates, diketimines, picolinates, N-alkoxypyrazoles, and deuterated analogs thereof.

Monodentate ligand L3 can be anionic or nonionic. Anionic ligands include, but are not limited to, H⁻ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L2, such as β-enolates and phosphinoakoxides, can act as monodentate ligands. The monodentate ligand can also be a coordinating anion such as halide, cyanide, isocyanide, nitrate, sulfate, hexahaloantimonate, and the like. These ligands are generally available commercially.

The monodentate L3 ligand can also be a non-ionic ligand, such as CO or a monodentate phosphine ligand.

The iridium complex dopants can be made using standard synthetic techniques as described in, for example, U.S. Pat. No. 6,670,645.

In some embodiments, the dopant is a small organic luminescent compound. In some embodiments, the dopant is selected from the group consisting of a non-polymeric spirobifluorene compound and a fluoranthene compound.

In some embodiments, the dopant is a compound having aryl amine groups. In some embodiments, the dopant is selected from the formulae below:

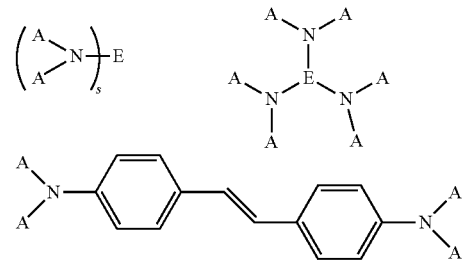

where:
A is the same or different at each occurrence and is selected from the group consisting of hydrocarbon aryl, heteroaryl, and deuterated analogs thereof;
E is a hydrocarbon aryl group or deuterated analog thereof; and
s is an integer from 1-6.

In some embodiments of the above formulae, E has at least three condensed rings.

In some embodiments of the above formulae, s=2.

In some embodiments, E is derived from a compound selected from the group consisting of naphthalene, anthracene, chrysene, pyrene, tetracene, xanthene, perylene, coumarin, rhodamine, quinacridone, benzofluorene, and rubrene.

In some embodiments, A is selected from the group consisting of phenyl, biphenyl, terphenyl, tolyl, naphthyl, naphthylphenyl, and anthracenyl groups.

In some embodiments, the dopant has the formula below:

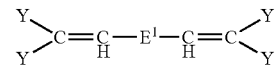

where:

Y is the same or different at each occurrence and is an aromatic group having 3-60 carbon atoms;

E¹ is an aromatic group, a divalent triphenylamine residue group, or a single bond.

In some embodiments, the dopant is an aryl acene. In some embodiments, the dopant is a non-symmetrical aryl acene.

In some embodiments, the small molecule organic dopant is selected from the group consisting of amino-substituted chrysenes, amino-substituted anthracenes, amino-substituted benzofluorenes, amino-substituted pyrenes, and deuterated analogs thereof.

In some embodiments of the composition, the dopant is capable of electroluminescence having an emission maximum between approximately 600 and 750 nm. Such materials are herein referred to as "red light-emitting materials" or "red light-emitting dopants".

Examples of red light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

Examples of red light-emitting organometallic iridium complexes include, but are not limited to compounds D1 through D10 below D1
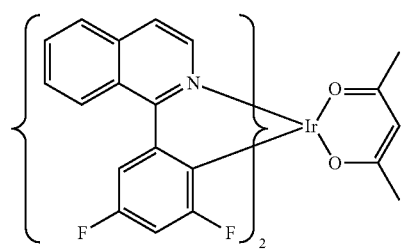

D2
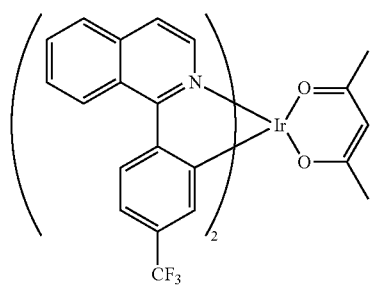

D3
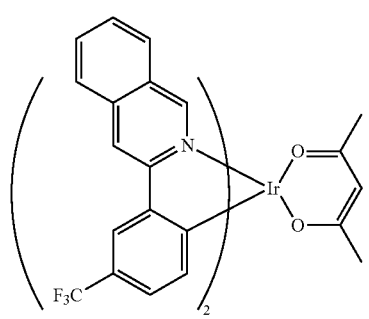

D4
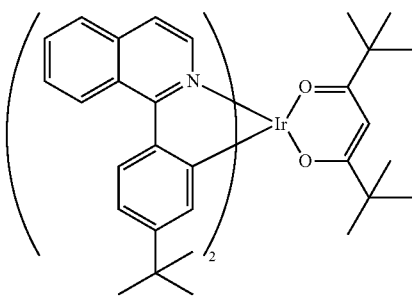

D5
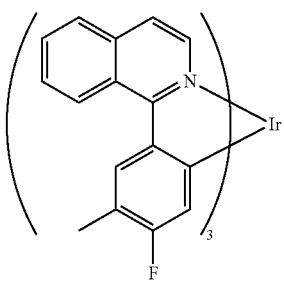

D6
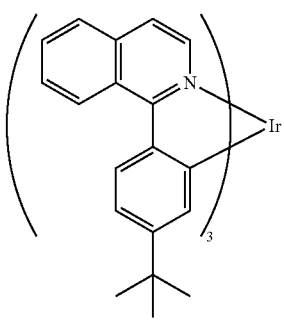

D7
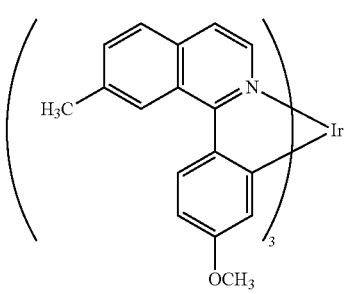

D8
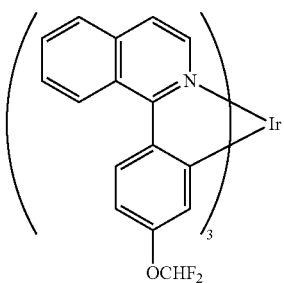

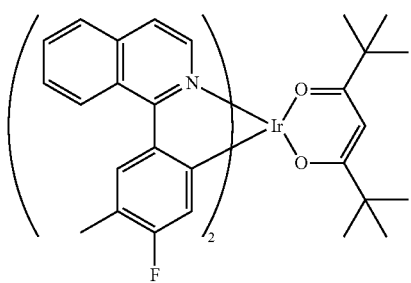

D9

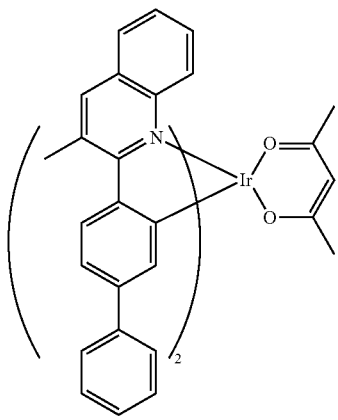

D10

In some embodiments of the composition, the dopant is capable of electroluminescence having an emission maximum between approximately 495 and 600 nm. Such materials are herein referred to as "green light-emitting materials" or "green light-emitting dopants".

In some embodiments, the green light-emitting materials have an emission maximum between 495 and 570 nm.

In some embodiments, the green light-emitting material is more yellow in color and has an emission maximum between approximately 570 and 590 nm. Such materials are herein referred to as "yellow light-emitting materials" or "yellow light-emitting dopants".

Examples of green light-emitting materials include, but are not limited to, complexes of Ir having phenylpyridine ligands, bis(diarylamino)anthracenes, and polyphenylenevinylene polymers. Green light-emitting materials have been disclosed in, for example, published PCT application WO 2007/021117.

Examples of green light-emitting organometallic Ir complexes include, but are not limited to, D11 through D33 below.

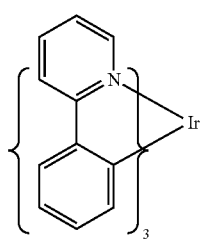

D11

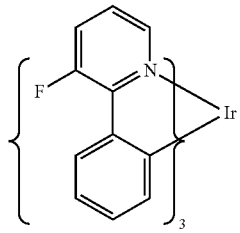

D12

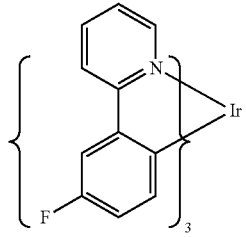

D13

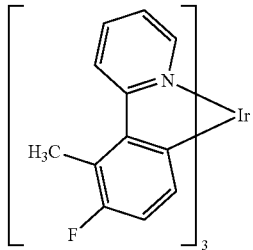

D14

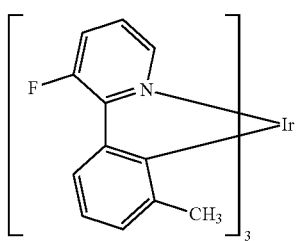

D15

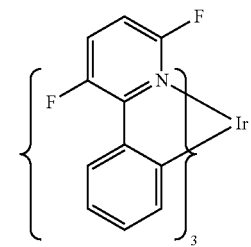

D16

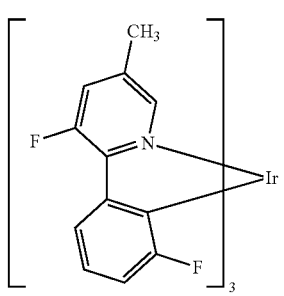

D17

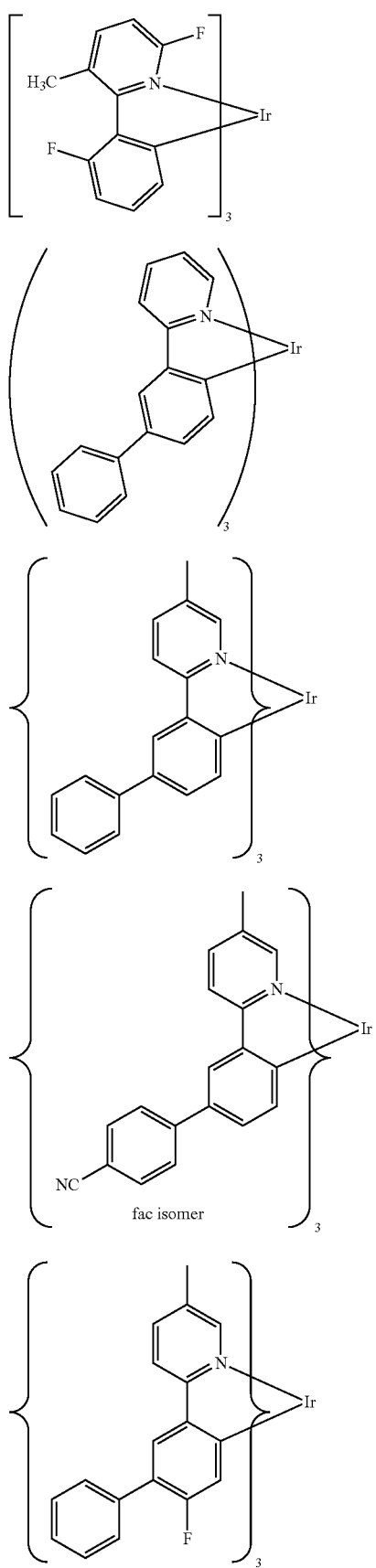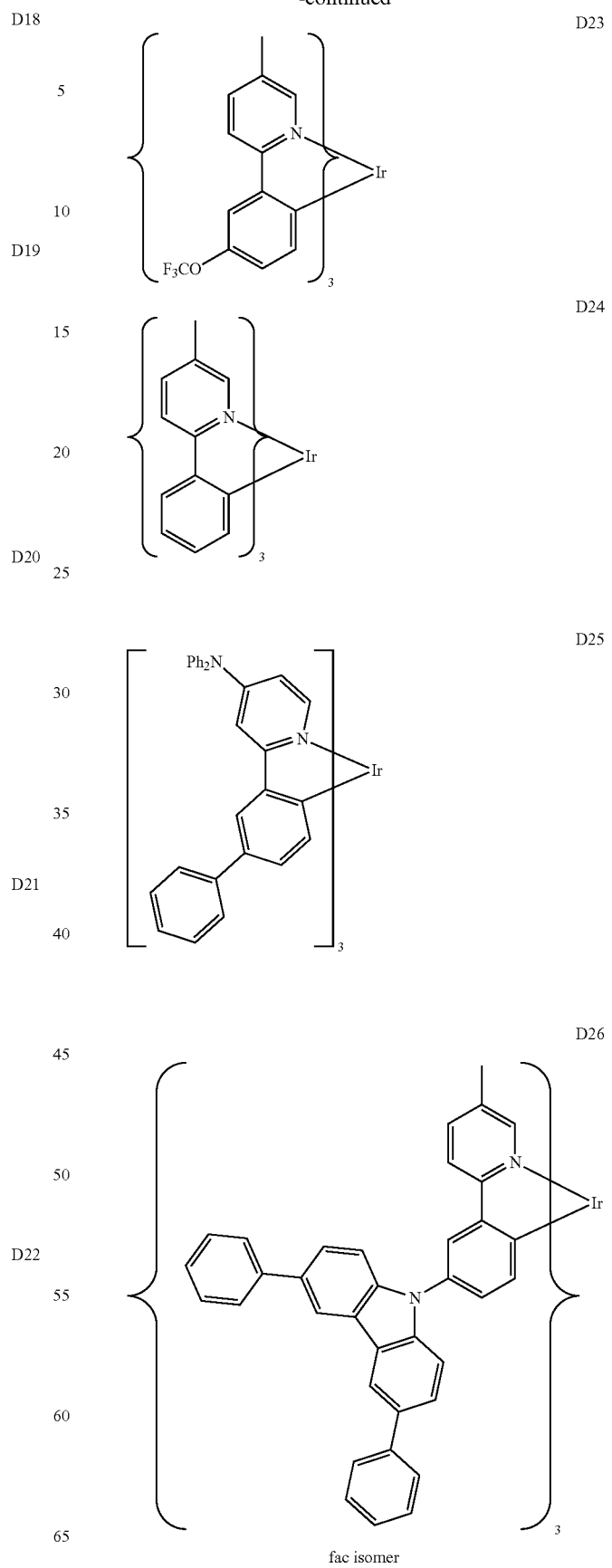

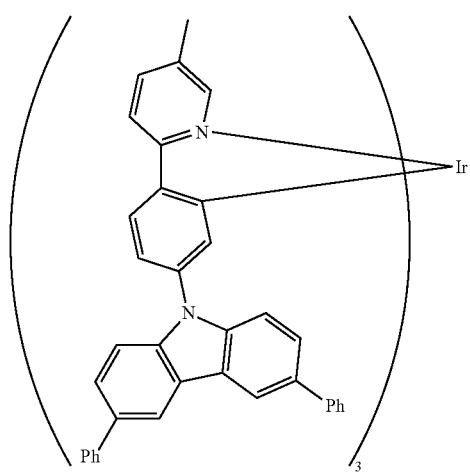
D27
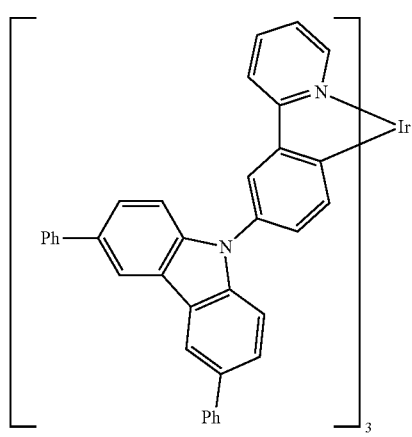
D28
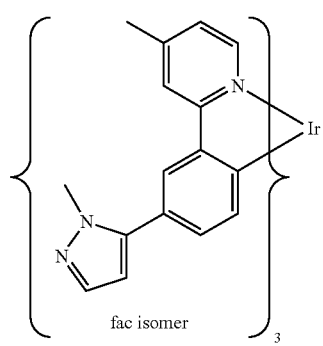
D29
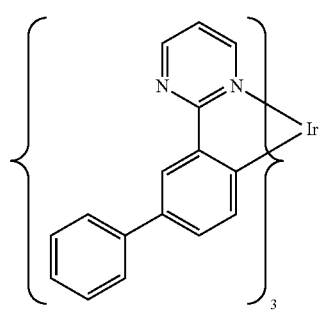
D30
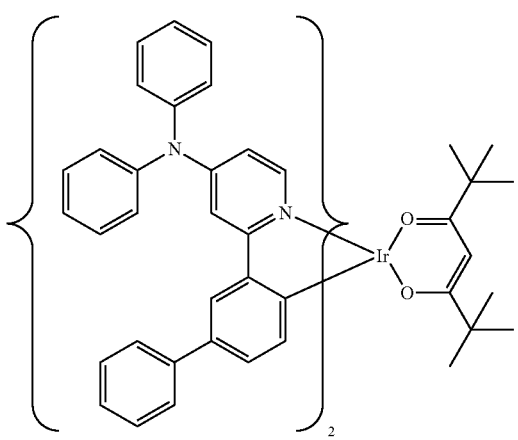
D31
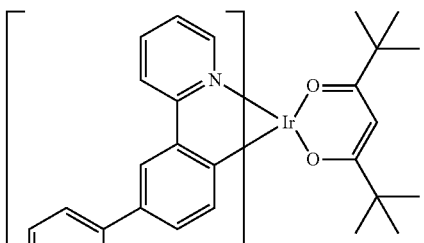
D32
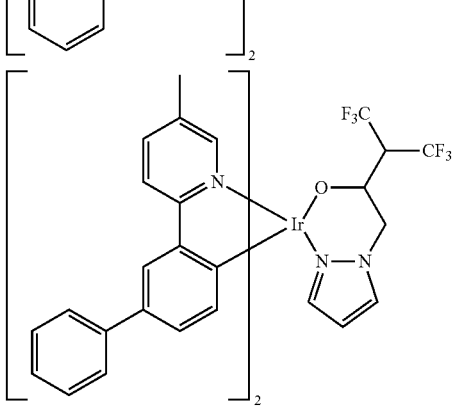
D33
Some examples of small molecule organic green light-emitting materials include, but are not limited to, compounds D52 through D59 shown below.
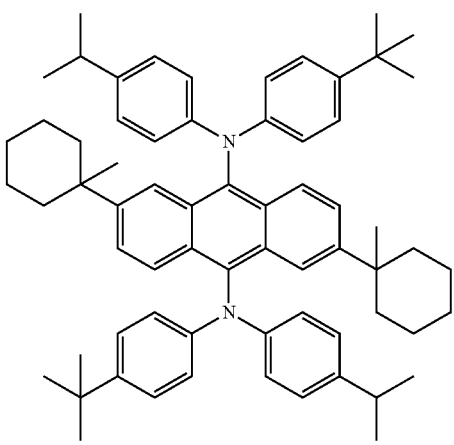
D52

-continued
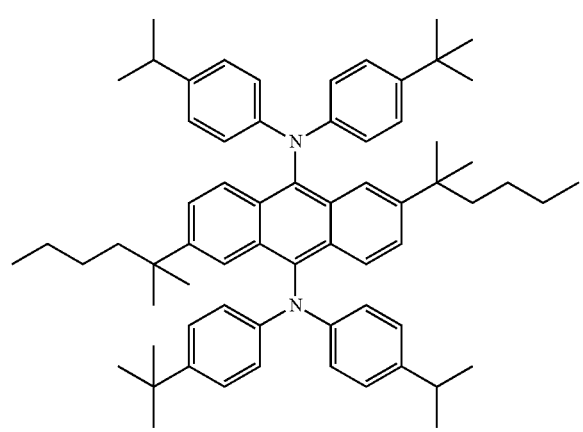
D53
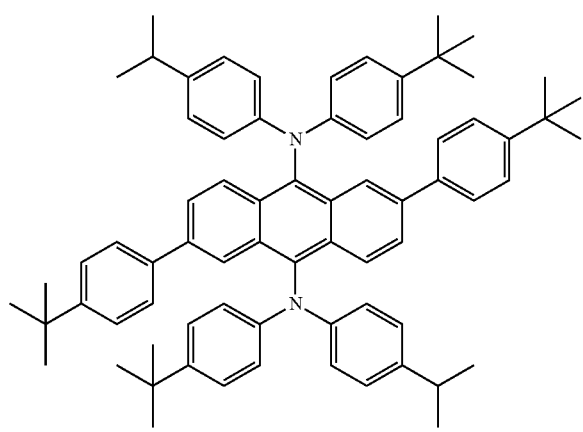
D54
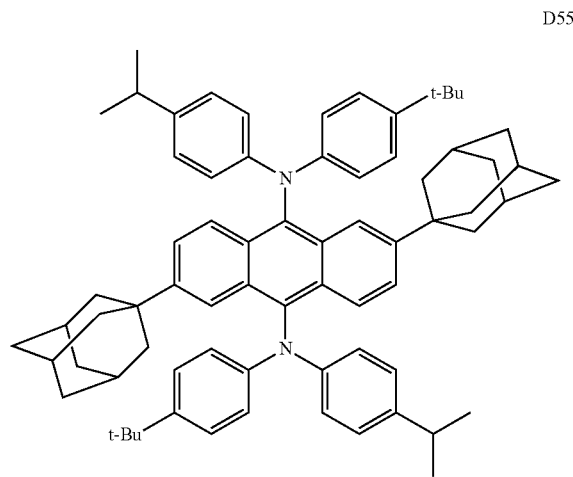
D55
-continued
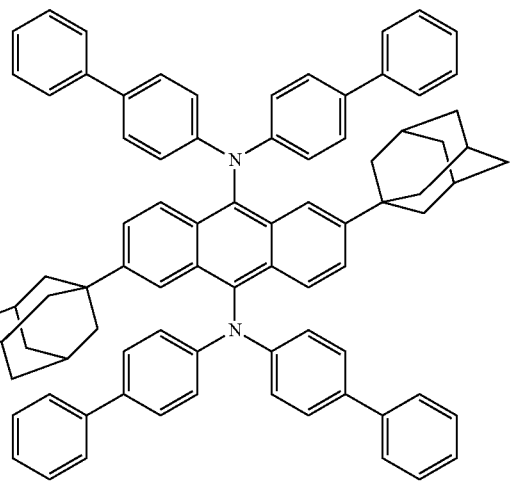
D56
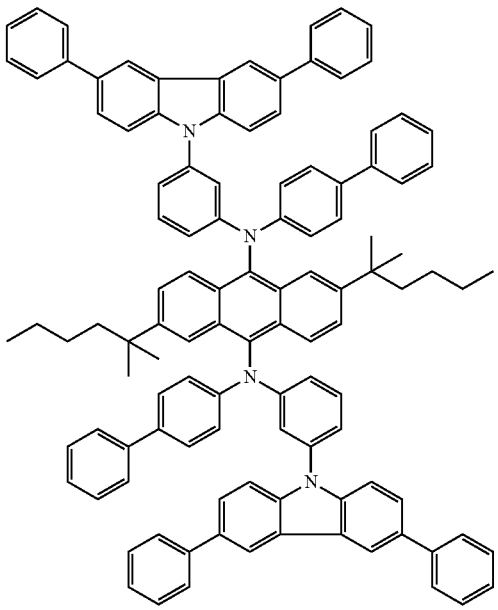
D57
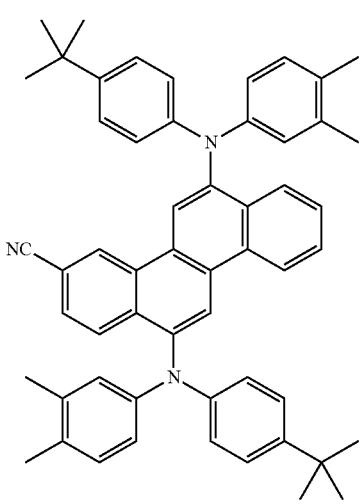
D58

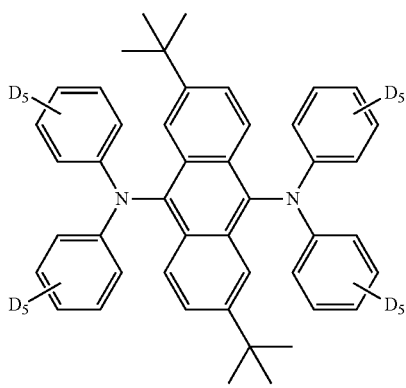

D59

In some embodiments of the composition, the dopant is capable of electroluminescence having an emission maximum between approximately 380 and 495 nm. Such materials are herein referred to as "blue light-emitting materials" or "blue light-emitting dopants".

In some embodiments, the blue light-emitting materials have an emission maximum between 450 and 495 nm.

Examples of blue light-emitting materials include, but are not limited to, complexes of Ir having phenylpyridine or phenylimidazole ligands, diarylanthracenes, diaminochrysenes, diaminopyrenes, diaminobenzofluorenes, and polyfluorene polymers. Blue light-emitting materials have been disclosed in, for example, U.S. Pat. No. 6,875,524, and published US applications 2007-0292713 and 2007-0063638.

Examples of blue light-emitting organometallic Ir complexes include, but are not limited to, D34 through D51 below.

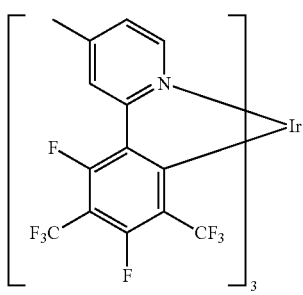

D34

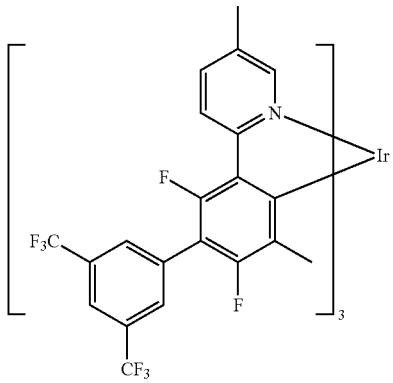

D35

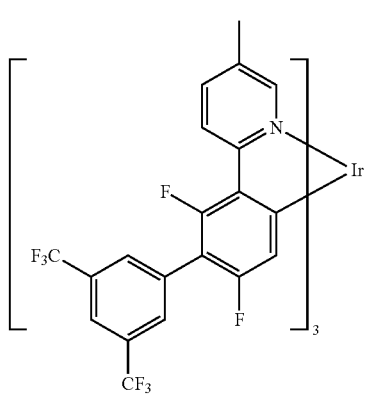

D36

D37

D38

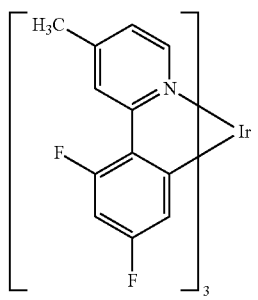

D39

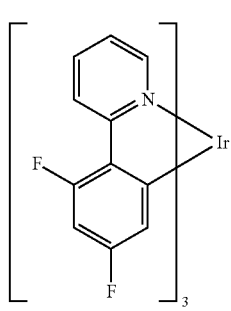

D40

D41 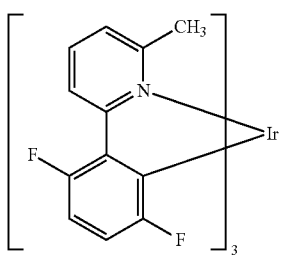
D42 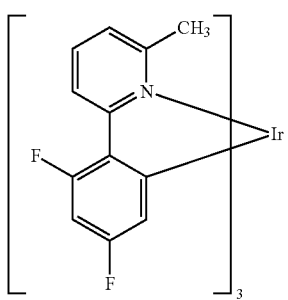
D43 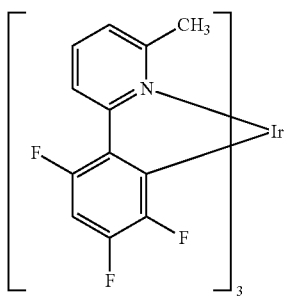
D44 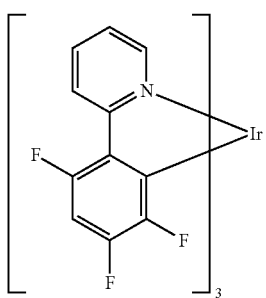
D45 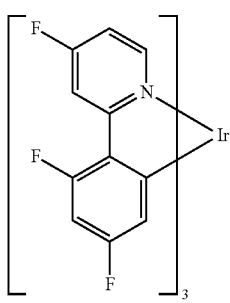
D46 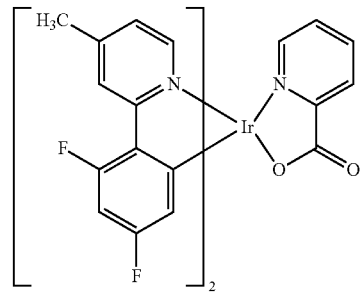
D47 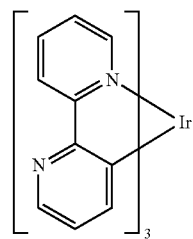
D48 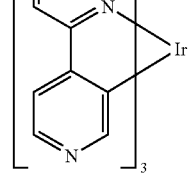
D49 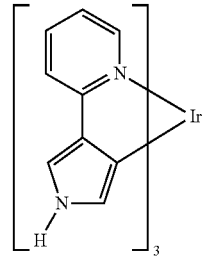
D50 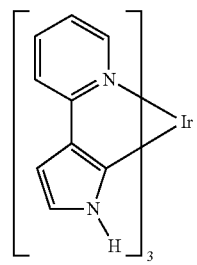
D51 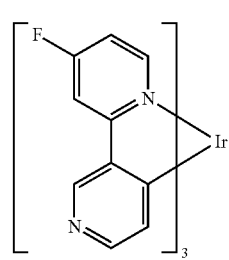

Examples of small molecule organic blue light-emitting materials include, but are not limited to compounds D60 through D68 shown below.
D60
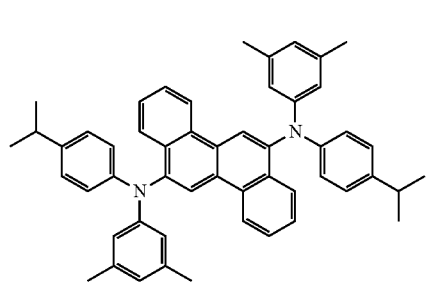
D61
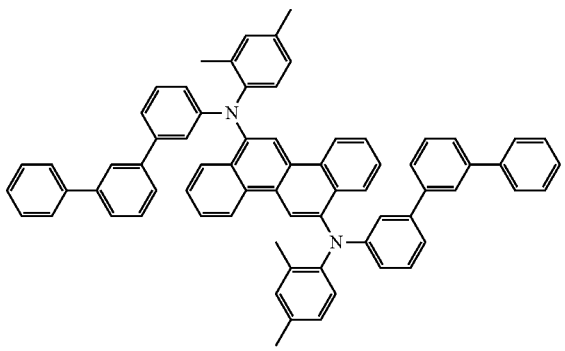
D62
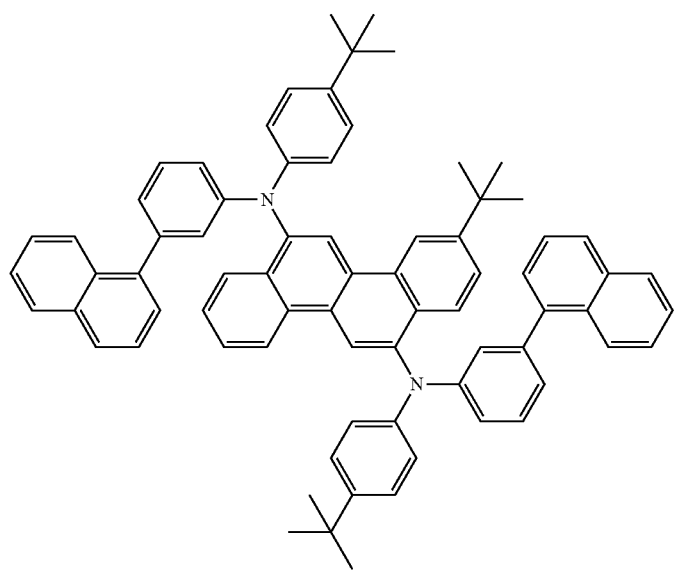
D63
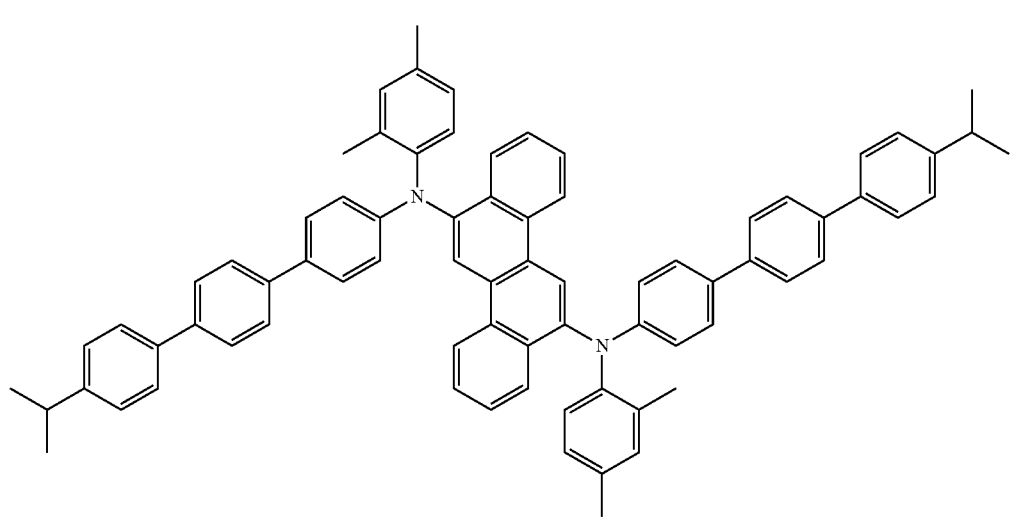

-continued
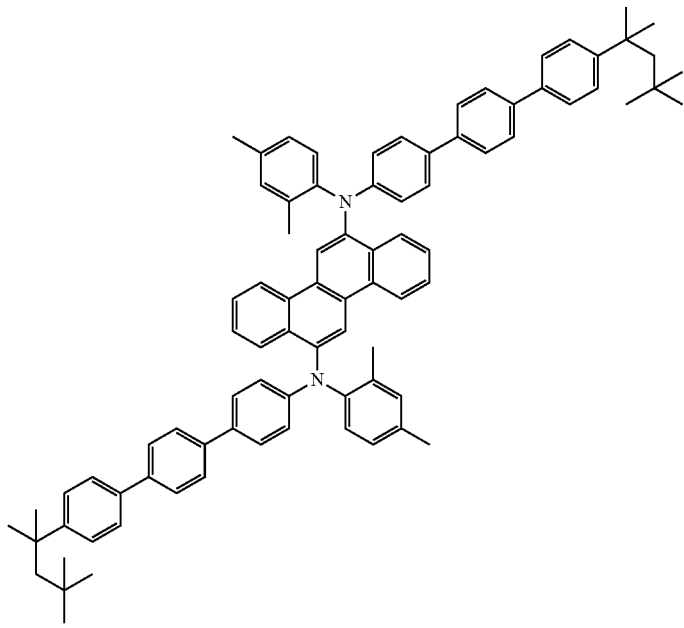
D64
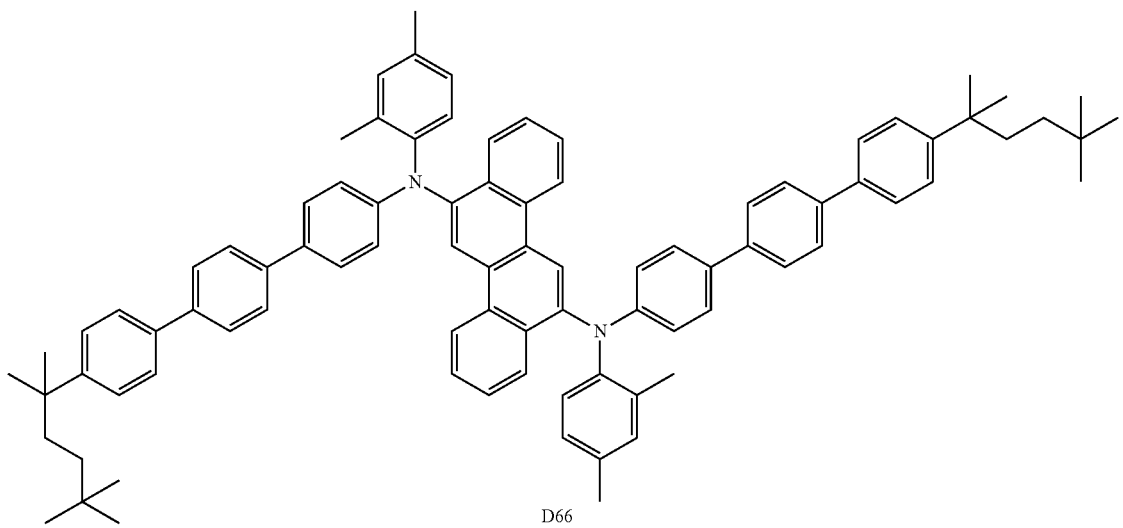
D65
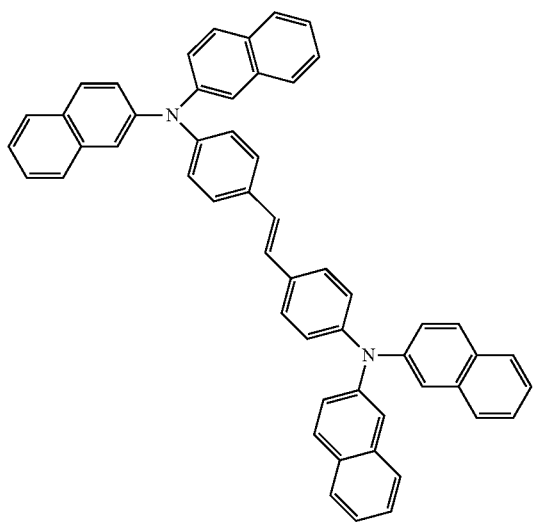
D66
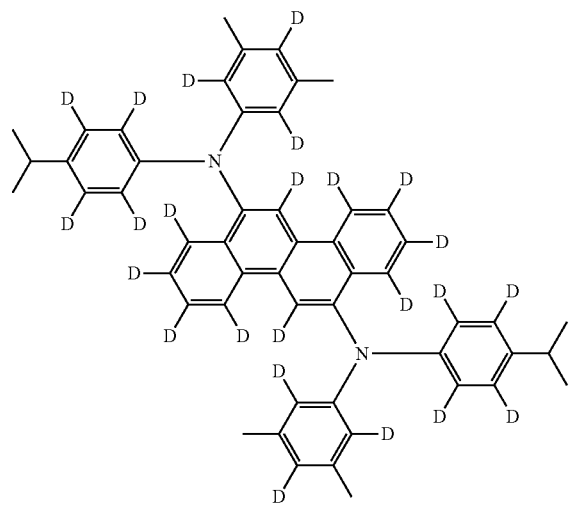
D67

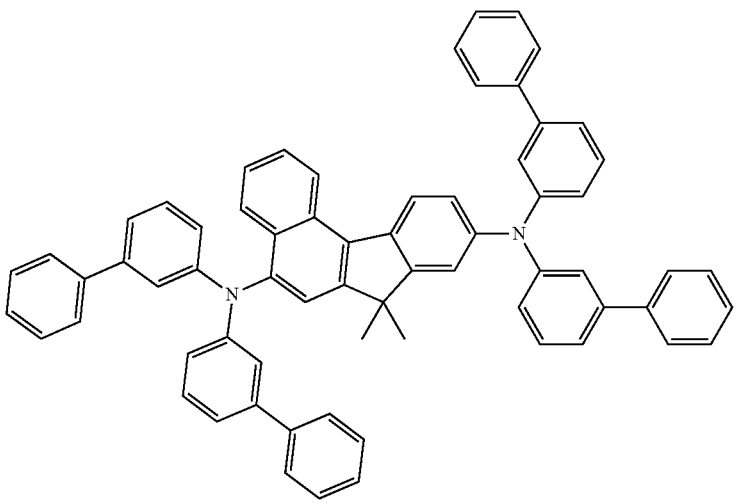

D68

(b) First Host

The first host compound is an N-heterocycle having at least one substituent of Formula I, as described in detail above.

(c) Second Host

In some embodiments, the second host is deuterated. In some embodiments, the second host is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated. In some embodiments, the second host is 100% deuterated.

Examples of second host materials include, but are not limited to, carbazoles, indolocarbazoles, chrysenes, phenanthrenes, triphenylenes, phenanthrolines, triazines, naphthalenes, anthracenes, quinolines, isoquinolines, quinoxalines, phenylpyridines, benzodifurans, dibenzofurans, benzodifurans, metal quinolinate complexes, substituted derivatives thereof, and deuterated analogs thereof.

In some embodiments, the second host is selected from the group consisting of indolocarbazoles, chrysenes, triphenylenes, dibenzofurans, benzodifurans, substituted derivatives thereof, and deuterated analogs thereof.

In some embodiments, the second host is selected from the group consisting of indolocarbazoles, chrysenes, substituted derivatives thereof, and deuterated analogs thereof.

In some embodiments, the second host has one of Formula V(a), Formula V(b), Formula V(c), Formula V(d), and Formula V(e)

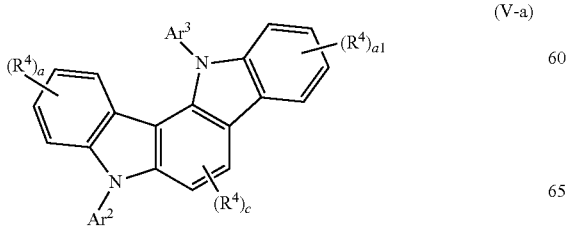
(V-a)

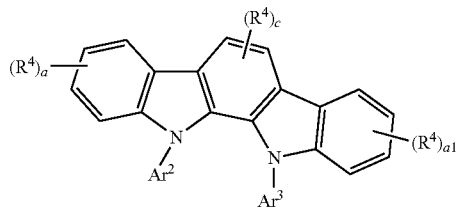
(V-b)

(V-c)

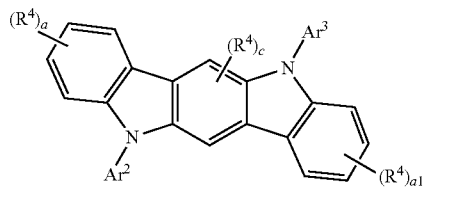
(V-d)

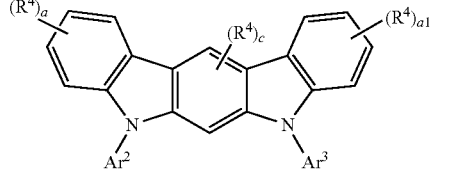
(V-e)

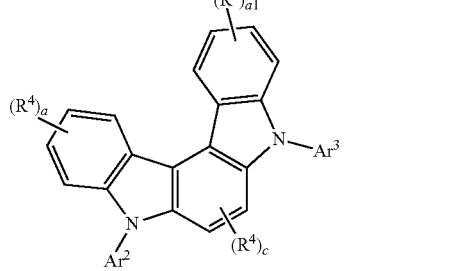

wherein:
Ar$^2$ and Ar$^3$ are the same or different and are hydrocarbon aryl or deuterated hydrocarbon aryl groups;
R$^4$ is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent $R^4$ groups can be joined together to form a fused ring;

a and a1 are the same or different and are an integer from 0-4; and c is an integer from 0-2.

In some embodiments, the second host has Formula V-a.
In some embodiments, the second host has Formula V-b.
In some embodiments, the second host has Formula V-c.
In some embodiments, the second host has Formula V-d.
In some embodiments, the second host has Formula V-e.

In some embodiments of Formulae V-a through V-e, $Ar^2$ is a hydrocarbon aryl or deuterated analog thereof having 6-24 ring carbons.

In some embodiments of Formulae V-a through V-e, $Ar^2$ has Formula a, as defined above.

In some embodiments of Formulae V-a through V-e, $Ar^2$ has Formula b, defined above.

In some embodiments of Formulae V-a through V-e, $Ar^2$ is a hydrocarbon aryl having no non-aromatic substituents.

In some embodiments of Formulae V-a through V-e, $Ar^2$ is a deuterated hydrocarbon aryl having no other substituents.

In some embodiments of Formulae V-a through V-e, $Ar^2$ is a substituted hydrocarbon aryl. In some embodiments, the substituents are selected from the group consisting of D, alkyl, alkoxy, silyl, germyl, deuterated alkyl, deuterated alkoxy, deuterated silyl, deuterated germyl, and combinations thereof.

In some embodiments of Formulae V-a through V-e, $Ar^2$ is selected from the group consisting of phenyl, naphthyl, biphenyl, binaphthyl, terphenyl, substituted derivatives thereof, and deuterated analogs thereof.

All of the above-described embodiments for $Ar^2$ apply equally to $Ar^3$.

In some embodiments of Formulae V-a through V-e, a=0.
In some embodiments of Formulae V-a through V-e, a=1.
In some embodiments of Formulae V-a through V-e, a=2.
In some embodiments of Formulae V-a through V-e, a=3.
In some embodiments of Formulae V-a through V-e, a=4.
In some embodiments of Formulae V-a through V-e, a>0.
In some embodiments of Formulae V-a through V-e, a>0 and at least one $R^4$=D.
In some embodiments of Formulae V-a through V-e, a>0 and at least one $R^4$ is an alkyl or deuterated alkyl having 1-12 carbon atoms.
In some embodiments of Formulae V-a through V-e, a>0 and at least one $R^4$ is a hydrocarbon aryl or deuterated hydrocarbon aryl having 6-24 ring carbons.
In some embodiments of Formulae V-a through V-e, a>0 and at least one $R^4$ is a hydrocarbon aryl having no non-aromatic substituents.
In some embodiments of Formulae V-a through V-e, a>0 and at least one $R^4$ is a deuterated hydrocarbon aryl having no other substituents.
In some embodiments of Formulae V-a through V-e, a>0 and at least one $R^4$ has Formula a, as defined above.
In some embodiments of Formulae V-a through V-e, a>0 and at least one $R^4$ has Formula b, as defined above.
In some embodiments of Formulae V-a through V-e, a>0 and at least one $R^4$ is selected from the group consisting of phenyl, naphthyl, biphenyl, substituted derivatives thereof, and deuterated analogs thereof. In some embodiments, the substituents are selected from the group consisting of D, alkyl, alkoxy, silyl, germyl, deuterated alkyl, deuterated alkoxy, deuterated silyl, deuterated germyl, and combinations thereof.

In some embodiments of Formulae V-a through V-e, a1=0.
In some embodiments of Formulae V-a through V-e, a1=1.
In some embodiments of Formulae V-a through V-e, a1=2.
In some embodiments of Formulae V-a through V-e, a1=3.
In some embodiments of Formulae V-a through V-e, a1=4.
In some embodiments of Formulae V-a through V-e, a1>0.
In some embodiments of Formulae V-a through V-e, a1>0 and at least one $R^4$ is as described above.

In some embodiments of Formulae V-a through V-e, c=0.
In some embodiments of Formulae V-a through V-e, c=1.
In some embodiments of Formulae V-a through V-e, c>0.
In some embodiments of Formulae V-a through V-e, c>0 and $R^4$=D.

In some embodiments, the second host has Formula VI

wherein:
Ar$^4$ is selected from the group consisting of hydrocarbon aryls having at least two fused rings, heteroaryls having at least two fused rings, substituted derivatives thereof, and deuterated analogs thereof;

Ar$^5$ and Ar$^6$ are the same or different at each occurrence and are selected from the group consisting of hydrocarbon aryls, heteroaryls, substituted derivatives thereof, and deuterated analogs thereof; and m is 1 or 2.

In some embodiments of Formula VI, Ar$^4$ has 3-5 fused aromatic rings.

In some embodiments of Formula VI, Ar$^4$ is selected from the group consisting of anthracenes, chrysenes, pyrenes, phenanthrenes, triphenylenes, phenanthrolines, naphthalenes, anthracenes, quinolines, isoquinolines, quinoxalines, phenylpyridines, dibenzofurans, difuranobenzenes, substituted derivatives thereof, and deuterated analogs thereof.

In some embodiments of Formula VI, Ar$^4$ is selected from the group consisting of anthracenes, chrysenes, pyrenes, phenanthrenes, triphenylenes, substituted derivatives thereof, and deuterated analogs thereof.

In some embodiments of Formula VI, Ar$^5$=Ar$^6$.
In some embodiments of Formula VI, Ar$^5$≠Ar$^6$.
In some embodiments of Formula VI, Ar$^5$ is a hydrocarbon aryl or deuterated analog thereof. In some embodiments, the hydrocarbon aryl has 6-24 ring carbons.
In some embodiments of Formula VI, Ar$^5$ has Formula a, as defined above.
In some embodiments of Formula VI, Ar$^5$ has Formula b, as defined above.
In some embodiments of Formula VI, Ar$^5$ is a hydrocarbon aryl having no non-aromatic substituents.
In some embodiments of Formula VI, Ar$^5$ is a deuterated hydrocarbon aryl having no other substituents.
In some embodiments of Formula VI, Ar$^5$ is a substituted hydrocarbon aryl. In some embodiments, the substituents are selected from the group consisting of D, alkyl, alkoxy, silyl, germyl, deuterated alkyl, deuterated alkoxy, deuterated silyl, deuterated germyl, and combinations thereof.

In some embodiments of Formula VI, $Ar^5$ is selected from the group consisting of phenyl, naphthyl, biphenyl, binaphthyl, terphenyl, phenanthryl, anthracenyl, 4-naphthylphenyl, 4-phenanthrylphenyl, substituted derivatives thereof, and deuterated analogs thereof.

All of the above-described embodiments for $Ar^5$ apply equally to $Ar^6$.

In some embodiments of Formula VI, m=1.
In some embodiments of Formula VI, m=2.
In some embodiments, the second host has Formula VII

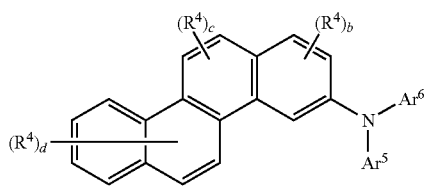

(VII)

wherein:
Ar$^5$ and Ar$^6$ are the same or different and are selected from the group consisting of hydrocarbon aryls, heteroaryls, substituted derivatives thereof, and deuterated analogs thereof;
R$^4$ is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent R$^4$ groups can be joined together to form a fused ring;
b is an integer from 0-3;
c is an integer from 0-2; and
d is an integer from 0-6.

In some embodiments of Formula VII, b=0.
In some embodiments of Formula VII, b=1.
In some embodiments of Formula VII, b=2.
In some embodiments of Formula VII, b=3.
In some embodiments of Formula VII, b>0.
In some embodiments of Formula VII, d>0 and at least one R$^4$ is D.
In some embodiments of Formula VII, d>0 and at least one R$^4$ is an alkyl having 1-12 carbons or a deuterated analog thereof.
In some embodiments of Formula VII, d>0 and at least one R$^4$ is a hydrocarbon aryl having 6-20 ring carbons or a deuterated analog thereof.
In some embodiments of Formula VII, c=0.
In some embodiments of Formula VII, c=1.
In some embodiments of Formula VII, c=2.
In some embodiments of Formula VII, c>0.
In some embodiments of Formula VII, c>0 and at least one R$^4$ is as described above.
In some embodiments of Formula VII, d=0.
In some embodiments of Formula VII, d=1.
In some embodiments of Formula VII, d=2.
In some embodiments of Formula VII, d=3.
In some embodiments of Formula VII, d=4.
In some embodiments of Formula VII, d=5.
In some embodiments of Formula VII, d=6.
In some embodiments of Formula VII, d>0.
In some embodiments of Formula VII, d>0 and at least one R$^4$ is as described above.

The above-described embodiments for Ar$^5$ and Ar$^6$ in Formula VI apply equally to Ar$^5$ and Ar$^6$ in Formula VII.

In some embodiments of the new composition, the first host is present in higher concentration than the second host, based on weight in the composition.

In some embodiments of the new composition, the weight ratio of first host to second host is in the range of 10:1 to 1:10. In some embodiments, the weight ratio is in the range of 6:1 to 1:6; in some embodiments, 5:1 to 1:2; in some embodiments, 3:1 to 1:1.

In some embodiments of the new composition, the weight ratio of dopant to the sum of first host and second host ("total host") is in the range of 1:99 to 20:80; in some embodiments, 5:95 to 15:85.

In some embodiments, the new composition is dissolved or dispersed in a liquid medium to form an ink. The ink can be used for liquid deposition of the materials to form layers.

The term "liquid medium" is intended to mean a liquid material, including a pure liquid, a combination of liquids, a solution, a dispersion, a suspension, and an emulsion. Liquid medium is used regardless whether one or more solvents are present.

In some embodiments, the liquid medium is a polar non-aqueous solvent. Examples of polar solvents include, but are not limited to, $C_1$ to $C_{20}$ alcohols, ethers, and acid esters.

In some embodiments, the liquid medium is relatively non-polar solvent. Examples of non-polar solvents include, but are not limited to $C_1$ to $C_{12}$ alkanes, aromatics such as toluene, xylenes, trifluorotoluene, and the like.

In some embodiments, the liquid medium is a mixture of two or more solvents.

In some embodiments, the liquid medium is selected from the group consisting of a chlorinated hydrocarbon (such as methylene chloride, chloroform, chlorobenzene), an aromatic hydrocarbon (such as a substituted or non-substituted toluene or xylene, including trifluorotoluene), a polar solvent (such as tetrahydrofuran (THF), N-methyl pyrrolidone (NMP)), an ester (such as ethylacetate, methylbenzoate, or diethylphthalate), an ether (such as anisole or dimethoxybenzene), an alcohol (such as isopropanol), a ketone (such as cyclopentanone), and any mixture thereof.

Suitable solvents for electroluminescent materials have been described in, for example, published PCT application WO 2007/145979.

4. Electronic Devices

Organic electronic devices that may benefit from having one or more layers including at least one compound as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), (4) devices that convert light of one wavelength to light of a longer wavelength, (e.g., a down-converting phosphor device); and (5) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure which can utilize the new compound described herein is shown in FIG. 1. The device 100 has a first electrical contact layer, an anode layer 110 and a second electrical contact layer, a cathode layer 160, and a photoactive layer 140 between them. Additional layers may optionally be present. Adjacent to the anode may be a hole injection layer 120, sometimes referred to as a buffer layer. Adjacent to the hole injection layer may be a hole transport layer 130, including hole transport material. Adjacent to the cathode may be an electron transport layer 150, including an electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the organic active layers.

Figure 2:
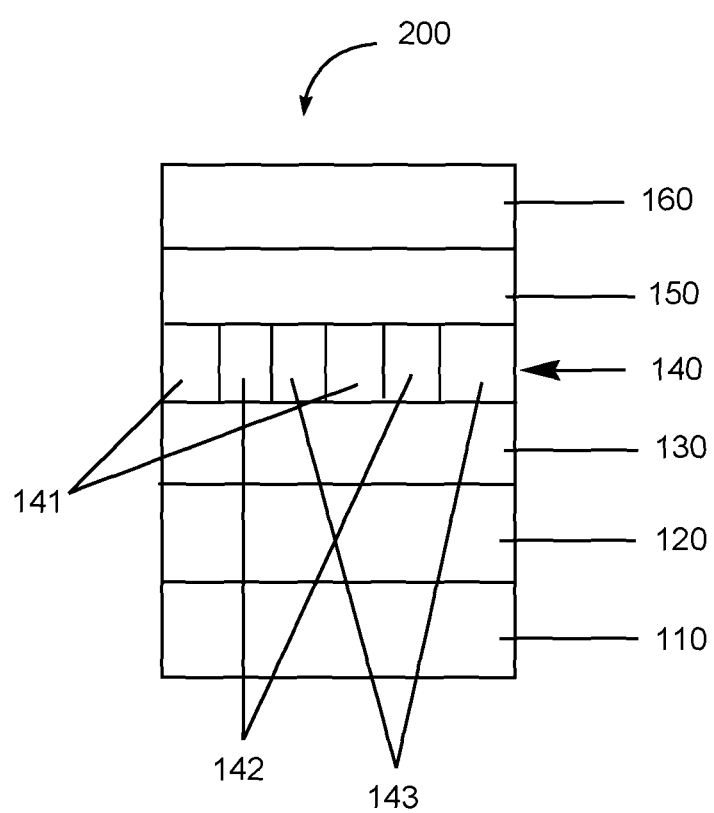
FIG. 2 includes an illustration of another example of an organic electronic device including the new compound described herein.

In some embodiments, in order to achieve full color, the light-emitting layer is pixelated, with subpixel units for each of the different colors. An illustration of a pixelated device is shown in FIG. 2. The device 200 has anode 110, hole injection layer 120, hole transport layer 130, photoactive layer 140, electron transport layer 150, and cathode 160. The photoactive layer is divided into subpixels 141, 142, 143, which are repeated across the layer. In some embodiments, the subpixels represent red, blue and green color emission. Although three different subpixel units are depicted in FIG. 2, two or more than three subpixel units may be used.

The different layers will be discussed further herein with reference to FIG. 1. However, the discussion applies to FIG. 2 and other configurations as well.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-3000 Å, in some embodiments, 200-2000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The desired ratio of layer thicknesses will depend on the exact nature of the materials used.

One or more of the new compounds comprising an N-heterocycle having at least one substituent of Formula I described herein may be present in one or more of the electroactive layers of a device.

In some embodiments, the new compounds comprising an N-heterocycle having at least one substituent of Formula I are useful as photoactive dopant materials in layer 140. In some embodiments, the new compounds comprising an N-heterocycle having at least one substituent of Formula I are present as photoactive dopant materials in one or more host materials.

In some embodiments, the new compounds comprising an N-heterocycle having at least one substituent of Formula I are useful as host materials for photoactive dopant materials in photoactive layer 140.

In some embodiments, the new compounds comprising an N-heterocycle having at least one substituent of Formula I are useful as electron transport material in electron transport layer 150.

In some embodiments, an organic electronic device includes an anode, a cathode, and at least one organic active layer therebetween, where the organic active layer includes a compound comprising an N-heterocycle having at least one substituent of Formula I.

In some embodiments, an organic electronic device includes an anode, a cathode, and a photoactive layer therebetween, where the photoactive layer includes a compound comprising an N-heterocycle having at least one substituent of Formula I.

In some embodiments, an organic electronic device includes an anode, a cathode, and a photoactive layer therebetween, where the photoactive layer includes (a) a dopant capable of electroluminescence having an emission maximum between 380 and 750 nm, (b) a first host compound which is an N-heterocycle having at least one substituent of Formula I, and (c) a second host compound.

In some embodiments, an organic electronic device includes an anode, a cathode, and a photoactive layer therebetween, and further includes an additional organic active layer including a compound comprising an N-heterocycle having at least one substituent of Formula I. In some embodiments, the additional organic active layer is a hole transport layer. In some embodiments, the additional organic active layer is an electron transport layer.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also include an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

Optional hole injection layer 120 includes hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer 120 can include charge transfer compounds, and the like, such as copper phthalocyanine and the tetrathiafulvalene-tetracyanoquinodimethane system (TTF-TCNQ). In some embodiments, the hole injection layer 120 is made from a dispersion of a conducting polymer and a colloid-forming polymeric acid. Such materials have been described in, for example, published U.S. patent applications 2004-0102577, 2004-0127637, and 2005-0205860.

Layer 130 includes hole transport material. Examples of hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4′,4″-tris(N,N-diphenyl-amino)-triphenylamine (TDATA); 4,4′,4″-tris(N-3-methylphenyl-N-phenyl-amino)-triphenylamine (MTDATA); N,N′-diphenyl-N,N′-bis(3-methylphenyl)-[1,1′-biphenyl]-4,4′-diamine (TPD); 4, 4′-bis(carbazol-9-yl)biphenyl (CBP); 1,3-bis(carbazol-9-yl)benzene (mCP); 1,1-bis[(di-4-tolylamino) phenyl]cyclohexane (TAPC); N,N′-bis(4-methylphenyl)-N,N′-bis(4-ethylphenyl)-[1,1′-(3,3′-dimethyl)biphenyl]-4,4′-diamine (ETPD); tetrakis-(3-methylphenyl)-N,N,N′,N′-2,5-phenylenediamine (PDA); α-phenyl-4-N,N-diphenylaminostyrene (TPS); p-(diethylamino)benzaldehyde diphenylhydrazone (DEH); triphenylamine (TPA); bis[4-(N,N-diethylamino)-2-methylphenyl](4-methylphenyl)methane (MPMP); 1-phenyl-3[p-(diethylamino)styryl]-5-[p-(diethylamino)phenyl]pyrazoline (PPR or DEASP); 1,2-trans-bis(9H-carbazol-9-yl)cyclobutane (DCZB); N,N,N′,N′-tetrakis(4-methylphenyl)-(1,1′-biphenyl)-4,4′-diamine (TTB); N,N′-bis(naphthalen-1-yl)-N,N′-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Depending upon the application of the device, the photoactive layer 140 can be a light-emitting layer that is activated by an applied voltage (such as in a light-emitting diode or light-emitting electrochemical cell), a layer of material that absorbs light and emits light having a longer wavelength (such as in a down-converting phosphor device), or a layer of material that responds to radiant energy and generates a signal with or without an applied bias voltage (such as in a photodetector or photovoltaic device).

In some embodiments, the photoactive layer includes a compound comprising an N-heterocycle having at least one substituent of Formula I as a photoactive material. In some embodiments, the photoactive layer further comprises a host material. Examples of host materials include, but are not limited to, chrysenes, phenanthrenes, triphenylenes, phenanthrolines, naphthalenes, anthracenes, quinolines, isoquinolines, quinoxalines, phenylpyridines, carbazoles, indolocarbazoles, furans, benzofurans, dibenzofurans, benzodifurans, and metal quinolinate complexes. In some embodiments, the host materials are deuterated.

In some embodiments, the photoactive layer includes a compound having Formula I as host material and additionally includes a photoactive dopant. Suitable photoactive dopants are described above.

In some embodiments, the photoactive layer comprises (a) a dopant capable of electroluminescence having an emission maximum between 380 and 750 nm, (b) a first host compound which is an N-heterocycle having at least one substituent of Formula I, and (c) a second host compound. Suitable second host compounds are described above.

In some embodiments, the photoactive layer includes only (a) a dopant capable of electroluminescence having an emission maximum between 380 and 750 nm, (b) a first host compound which is an N-heterocycle having at least one substituent of Formula I, and (c) a second host compound, where additional materials that would materially alter the principle of operation or the distinguishing characteristics of the layer are not present.

In some embodiments, the first host is present in higher concentration than the second host, based on weight in the photoactive layer.

In some embodiments, the weight ratio of first host to second host in the photoactive layer is in the range of 10:1 to 1:10. In some embodiments, the weight ratio is in the range of 6:1 to 1:6; in some embodiments, 5:1 to 1:2; in some embodiments, 3:1 to 1:1.

In some embodiments, the weight ratio of dopant to the total host is in the range of 1:99 to 20:80; in some embodiments, 5:95 to 15:85.

In some embodiments, the photoactive layer comprises (a) a red light-emitting dopant, (b) a first host compound which is an N-heterocycle having at least one substituent of Formula I, and (c) a second host compound having Formula VI, as defined above.

In some embodiments, the photoactive layer comprises (a) a red light-emitting dopant, (b) a first host compound which is an N-heterocycle having at least one substituent of Formula I, and (c) a second host compound having Formula VII, as defined above.

In some embodiments, the photoactive layer comprises (a) a green light-emitting dopant, (b) a first host compound which is an N-heterocycle having at least one substituent of Formula I, and (c) a second host compound having one of Formula V(a), Formula V(b), Formula V(c), Formula V(d), and Formula V(e), as defined above.

In some embodiments, the photoactive layer comprises (a) a green light-emitting dopant, (b) a first host compound which is an N-heterocycle having at least one substituent of Formula I, and (c) a second host compound having Formula V(a).

In some embodiments, the photoactive layer comprises (a) a green light-emitting dopant, (b) a first host compound which is an N-heterocycle having at least one substituent of Formula I, and (c) a second host compound having Formula V(b).

In some embodiments, the photoactive layer comprises (a) a green light-emitting dopant, (b) a first host compound which is an N-heterocycle having at least one substituent of Formula I, and (c) a second host compound having Formula V(c).

In some embodiments, the photoactive layer comprises (a) a green light-emitting dopant, (b) a first host compound which is an N-heterocycle having at least one substituent of Formula I, and (c) a second host compound having Formula V(d).

In some embodiments, the photoactive layer comprises (a) a green light-emitting dopant, (b) a first host compound which is an N-heterocycle having at least one substituent of Formula I, and (c) a second host compound having Formula V(e).

In some embodiments, the photoactive layer comprises (a) a yellow light-emitting dopant, (b) a first host compound which is an N-heterocycle having at least one substituent of Formula I, and (c) a second host compound having one of Formula V(a), Formula V(b), Formula V(c), Formula V(d), and Formula V(e), as defined above.

In some embodiments, the photoactive layer comprises (a) a yellow light-emitting dopant, (b) a first host compound which is an N-heterocycle having at least one substituent of Formula I, and (c) a second host compound having Formula V(a).

In some embodiments, the photoactive layer comprises (a) a yellow light-emitting dopant, (b) a first host compound which is an N-heterocycle having at least one substituent of Formula I, and (c) a second host compound having Formula V(b).

In some embodiments, the photoactive layer comprises (a) a yellow light-emitting dopant, (b) a first host compound which is an N-heterocycle having at least one substituent of Formula I, and (c) a second host compound having Formula V(c).

In some embodiments, the photoactive layer comprises (a) a yellow light-emitting dopant, (b) a first host compound which is an N-heterocycle having at least one substituent of Formula I, and (c) a second host compound having Formula V(d).

In some embodiments, the photoactive layer comprises (a) a yellow light-emitting dopant, (b) a first host compound which is an N-heterocycle having at least one substituent of Formula I, and (c) a second host compound having Formula V(e).

Optional layer 150 can function both to facilitate electron transport, and also serve as a confinement layer to prevent quenching of the exciton at layer interfaces. Preferably, this layer promotes electron mobility and reduces exciton quenching.

In some embodiments, layer 150 includes a compound comprising an N-heterocycle having at least one substituent of Formula I.

In some embodiments, layer 150 includes only a compound comprising an N-heterocycle having at least one substituent of Formula I, where additional materials that would materially alter the principle of operation or the distinguishing characteristics of the layer are not present. In some embodiments, layer 150 includes other electron transport materials. Examples of electron transport materials which can be used in the optional electron transport layer 150, include metal chelated oxinoid compounds, including metal quinolate derivatives such as tris(8-hydroxyquinolato) aluminum (AlQ), bis(2-methyl-8-quinolinolato)(p-phenylphenolato) aluminum (BAlq), tetrakis-(8-hydroxyquinolato) hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

An optional electron injection layer may be deposited over the electron transport layer. Examples of electron injection materials include, but are not limited to, Li-containing organometallic compounds, LiF, $Li_2O$, Li quinolate, Cs-containing organometallic compounds, CsF, $Cs_2O$, and $Cs_2CO_3$. This layer may react with the underlying electron transport layer, the overlying cathode, or both. When an electron injection layer is present, the amount of material deposited is generally in the range of 1-100 Å, in some embodiments 1-10 Å.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

For liquid deposition methods, a suitable solvent for a particular compound or related class of compounds can be readily determined by one skilled in the art. For some applications, it is desirable that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics such as toluene, xylenes, trifluorotoluene and the like. Other suitable liquids for use in making the liquid composition, either as a solution or dispersion as described herein, including the new compounds, includes, but not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methyl pyrrolidone) esters (such as ethylacetate) alcohols (isopropanol), ketones (cyclopentatone) and mixtures thereof. Suitable solvents for electroluminescent materials have been described in, for example, published PCT application WO 2007/145979.

In some embodiments, the device is fabricated by liquid deposition of the hole injection layer, the hole transport layer, and the photoactive layer, and by vapor deposition of the anode, the electron transport layer, an electron injection layer and the cathode.

It is understood that the efficiency of devices made with the new compositions described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In some embodiments, the device has the following structure, in order: anode, hole injection layer, hole transport layer, photoactive layer, electron transport layer, electron injection layer, cathode. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Synthesis Example 1

This example illustrates the preparation of Compound I-1.

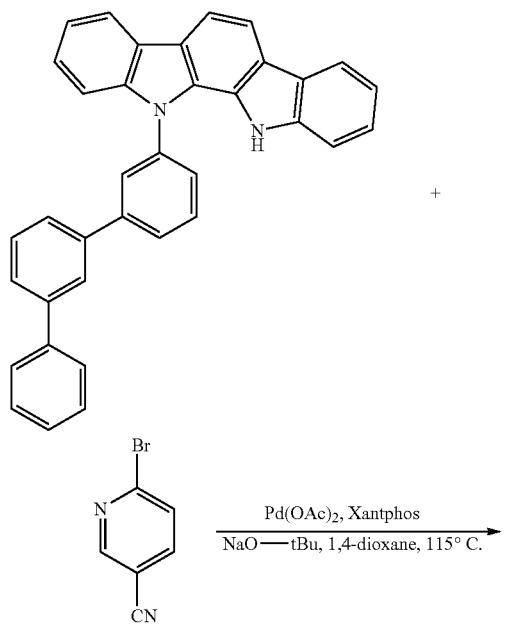

+

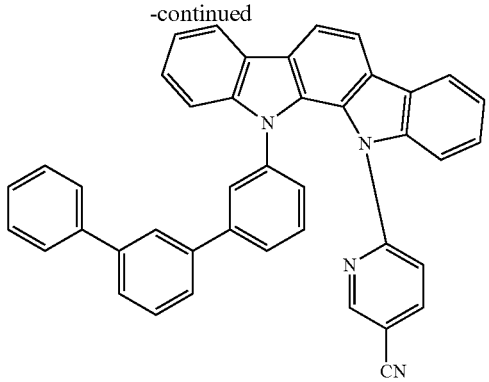

I-1

In a glove box, a mixture of 1.77 g of 2-bromo-5-cyanopyridine, 52 mg of Pd(OAc)$_2$, and 280 mg of 9,9-dimethyl-4,5-bis(diphenylphosphino)xanthene in 104 mL 1,4-dioxane was treated with 3.9 g of 12-[3-(3-phenylphenyl)phenyl]-11H-indolo[2,3-a]carbazole and 1.09 g of sodium tert-butoxide were added. The reaction was heated overnight at 115° C. The reaction mixture was cooled to room temperature, water was added, and the contents were extracted with dichloromethane. The combined organic layers were dried over sodium sulfate, filtered, and concentrated by rotary evaporation. The crude solid was dissolved in dichloromethane and purified by medium pressure liquid chromatography (MPLC) eluting with 80:20 to 30:70 hexanes:dichloromethane. The purest fractions were combined and concentrated by rotary evaporation to give the product as a yellow foam. Further purification of the material was accomplished by dissolving in toluene (10 mL) and passing through a 1" dia. plug of Florisil (100-200 mesh) (54 g), eluting with toluene (375 mL) then dichloromethane. The purest fractions were combined and concentrated by rotary evaporation. The product was dissolved in dichloromethane and methanol and carefully concentrated by rotary evaporation to give a solid which was filtered, washed with methanol, and concentrated under reduced pressure to remove the dichloromethane and give I-1 as a very light yellow solid (3.05 g, 64% yield, 99.99% pure by Ultra Performance Liquid Chromatography (UPLC)). Final purification prior to device preparation was accomplished by vacuum sublimation.

Synthesis Example 2

This example illustrates the preparation of Compound I-2.

a. Synthesis of 2-methylthio-4,6-diphenylpyrimidine-5-carbonitrile (Intermediate 1)

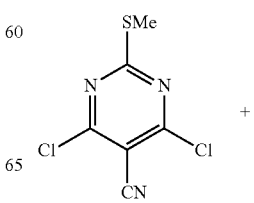

+

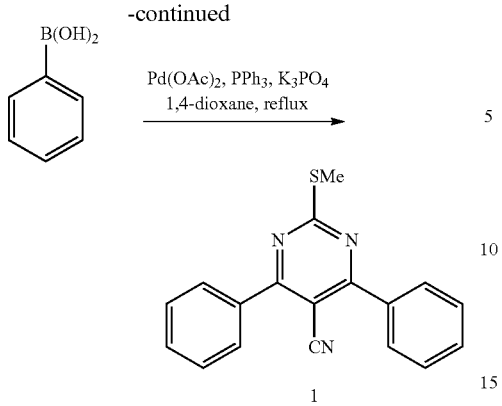

In a glove box, to 2.36 g of 4,6-dichloro-2-(methylthio)pyrimidine-5-carbonitrile in 500 mL of 1,4-dioxane was added 2.82 g of phenylboronic acid, 14.70 g of potassium phosphate, 60 mg of palladium (II) acetate, then 141 mg of triphenylphosphine. The reaction was refluxed under nitrogen for 2.25 hours, cooled to room temperature, and then concentrated by rotary evaporation. Water was added and the contents were extracted with dichloromethane. The combined organic layers were dried over sodium sulfate, filtered, and concentrated by rotary evaporation to give a solid which was triturated with 45 mL of a 2:1 mixture of methyl tert-butyl ether:dichloromethane, then washed with methyl tert-butyl ether to give Intermediate 1 as a tan solid (2.25 g, 65% yield).

b. Synthesis of 2-methylsulfonyl-4,6-diphenylpyrimidine-5-carbonitrile (Intermediate 2)

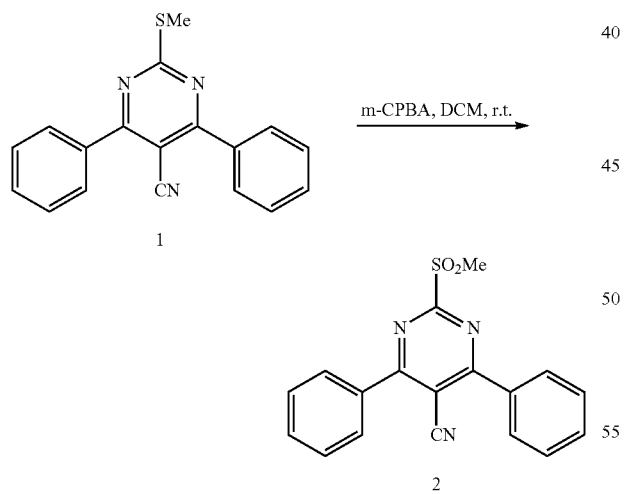

To 6.11 g of Intermediate 1 in 376 mL dichloromethane was added 11.75 g of m-chloroperbenzoic acid (77%) in 170 mL dichloromethane at room temperature over 5 minutes. After 2 hours, the reaction was washed with saturated aqueous sodium bicarbonate solution, then saturated sodium sulfite, then saturated aqueous sodium bicarbonate. The organic layer was isolated and stirred with 170 mL 1M NaHSO$_3$ and some 1,4-dioxane at room temperature for 90 minutes. The organic layer was isolated and the aq. layer was extracted with dichloromethane. The combined organic layers were dried over sodium sulfate, filtered, and concentrated by rotary evaporation. The resulting solid was triturated with 75 mL of 2:1 methyl tert-butyl ether:dichloromethane to give an off-white solid. The solid was dissolved in dichloromethane and purified by silica gel chromatography, eluting with dichloromethane to give, after combining and concentrating the purest fractions, Intermediate 2 as a white solid (5.4 g, 80% yield).

c. Synthesis of 2-hydroxy-4,6-diphenylpyrimidine-5-carbonitrile (Intermediate 3)

To 5.7 g of Intermediate 2 in 423 mL of 1,4-dioxane was added 34.0 mL of 1M aq. NaOH. After stirring the reaction at room temperature overnight, water (200 mL) was added and the pH adjusted with conc. aq. HCl until pH=2. The contents were extracted with dichloromethane and the combined organic layers were dried over sodium sulfate, filtered, and concentrated by rotary evaporation to give Intermediate 3 as a white solid (5.1 g, quantitative yield).

d. Synthesis of 2-chloro-4,6-diphenylpyrimidine-5-carbonitrile (Intermediate 4)

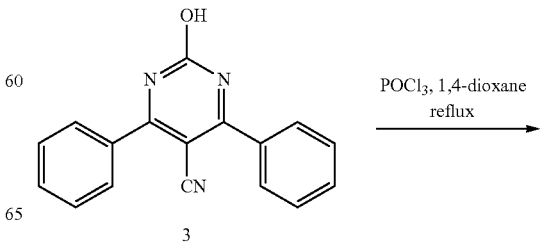

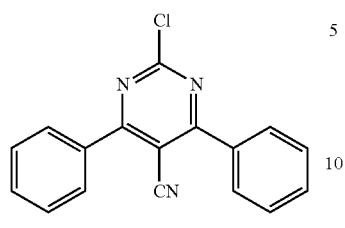

4

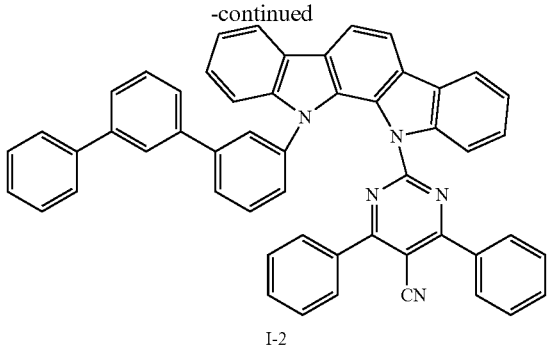

I-2

To a suspension of 5.1 g of Intermediate 3 in 97 mL of 1,4-dioxane was added 6.8 mL phosphorus oxychloride. The reaction was heated at reflux for one hour, cooled to room temperature, and water (300 mL) and sodium bicarbonate were added until basic. The contents were extracted with dichloromethane, and the combined organic layers were dried over sodium sulfate, filtered, and concentrated by rotary evaporation to provide an orange-white solid. The crude material was purified by MPLC, eluting with dichloromethane, combining the purest fractions to give, after concentration by rotary evaporation, Intermediate 4 as a white solid (3.2 g, 65% yield over 2 steps).

e. Synthesis of 11-(m-terphenyl)-12-(4,6-diphenyl-5-cyanopyrimidin-2-yl)-indolo[2,3-a]carbazole (I-2)

In a glove box, to 4.43 g of 12-[3-(3-phenylphenyl)phenyl]-11H-indolo[2,3-a]carbazole in 47 mL N,N-dimethylformamide at room temperature was added 436 mg of 60% NaH. After stirring for 50 minutes at room temperature, 3.2 g of Intermediate 4 in 127 mL N,N-diemthylformamide was added over 7 minutes. The reaction was heated at 54° C. overnight. The reaction mixture was cooled to room temperature, and water (400 mL) and saturated aqueous ammonium chloride (20 mL) were added. The contents were extracted with dichloromethane and the combined organic layers were dried over sodium sulfate, filtered, and concentrated by rotary evaporation. The crude material was purified by MPLC eluting with 90:10 to 50:50 hexanes:dichloromethane. The purest fractions were combined and concentrated to a residue that was dissolved in dichloromethane (30 mL). Acetonitrile (50 mL) was added and partial concentration by rotary evaporation provided, after filtration, more pure material. Recrystallization by dissolving in boiling dichloromethane (30 mL) and acetonitrile (34 mL) gave, after washing the collected solid with acetonitrile, I-2 as a yellow solid (2.55 g, 38% yield, 99.99% pure by UPLC).

Synthesis Example 3

This example illustrates the preparation of Compound I-3.

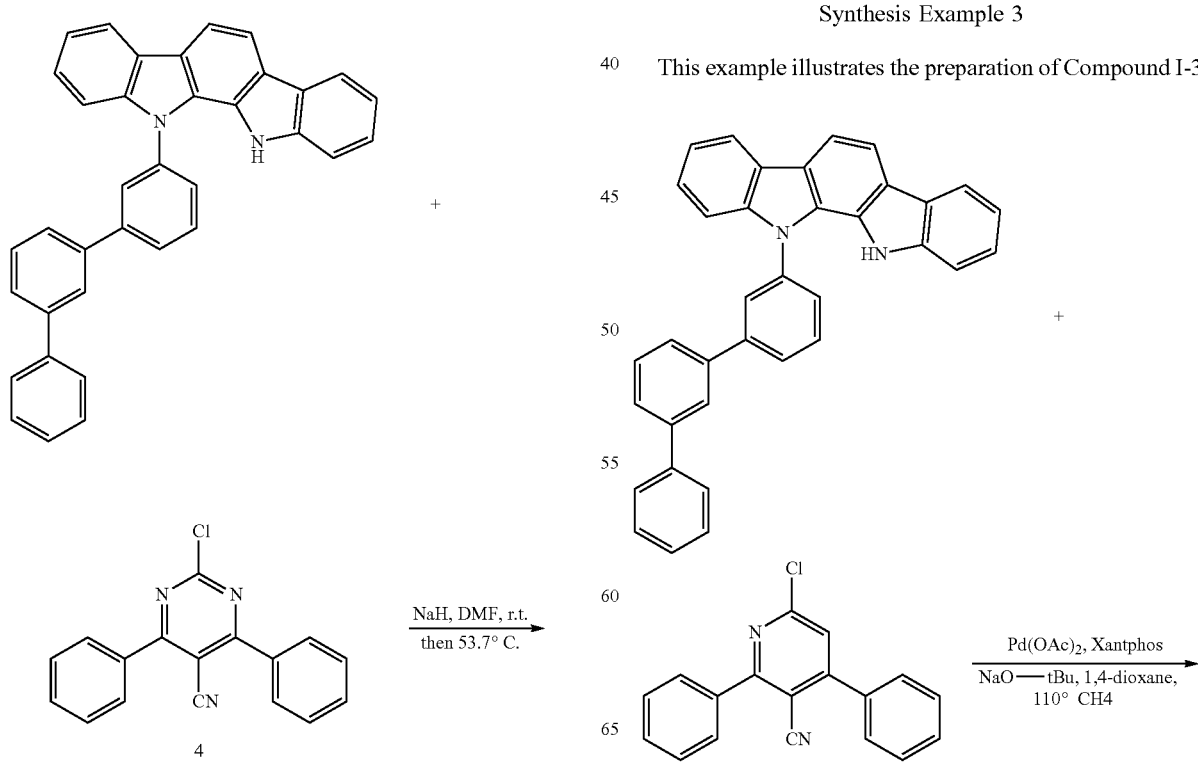

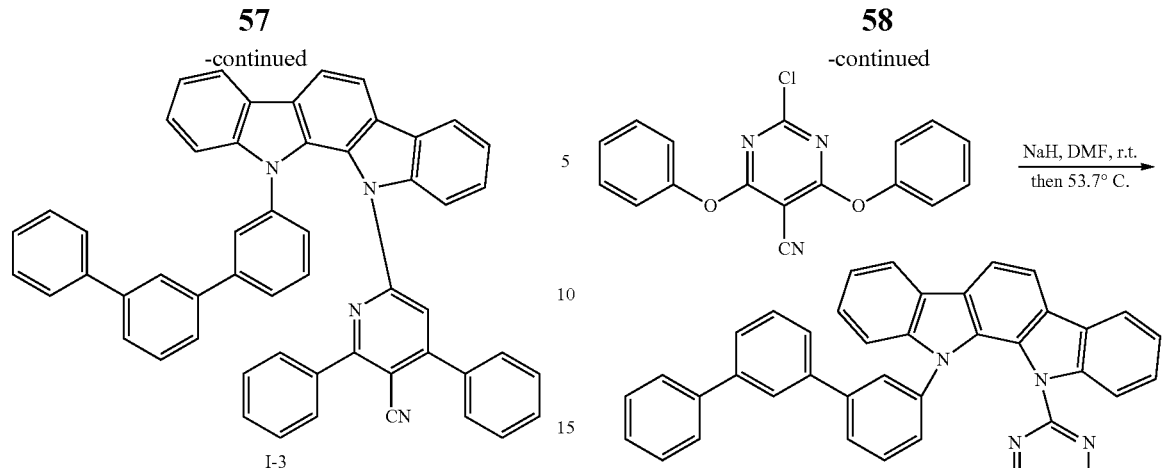

I-3

In a glove box, a mixture of 2.38 g of 2-chloro-4,6-diphenyl-5-cyanopyridine, 44 mg of palladium (II) acetate, and 237 mg of 9,9-dimethyl-4,5-bis(diphenylphosphino)-xanthene in 88 mL 1,4-dioxane was treated with 3.3 g of 12-[3-(3-phenylphenyl)phenyl]-11H-indolo[2,3-a]carbazole and 924 mg of sodium tert-butoxide. The reaction was heated at reflux for 10.5 hours. An additional 772 mg of 2-chloro-4,6-diphenyl-5-cyanopyridine in 3 mL 1,4-dioxane. After 1.5 hours of heating at reflux, 9 mg of palladium (II) acetate, 48 mg of 9,9-dimethyl-4,5-bis(diphenylphosphino)-xanthene, and 300 mg of sodium tert-butoxide were added. The reaction was heated at reflux for 4 hours. The reaction mixture was cooled to room temperature and the contents were extracted with dichloromethane, dried over sodium sulfate, filtered, and concentrated by rotary evaporation. The crude solid was dissolved in dichloromethane and purified by MPLC eluting with 85:15 to 50:50 hexanes:dichloriomethane. The purest fractions were combined and concentrated by rotary evaporation to give 1.87 g of the product as a very pale yellow solid. The solid was dissolved in sample 1:1dichloromethane:acetonitrile (60 mL) and partially concentrated until some solid precipitated. After an hour, the solid was filtered and washed with acetonitrile to give I-3 as a very pale yellow solid (1.40 g, 28% yield, 99.99% pure by UPLC). Final purification prior to device preparation was accomplished by vacuum sublimation.

Synthesis Example 4

This example illustrates the preparation of Compound I-4.

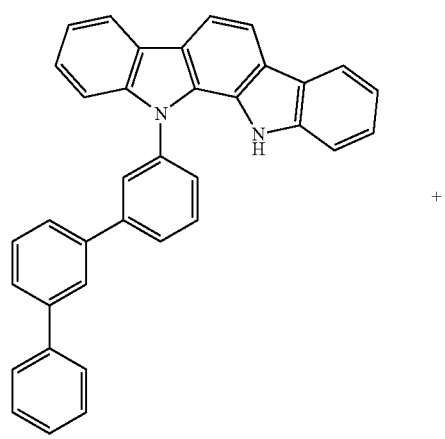

+

I-4

In a glove box, to 5.0 g of 12-[3-(3-phenylphenyl)phenyl]-11H-indolo[2,3-a]carbazole in 150 mL N,N-dimethylformamide at room temperature was added 496 mg of 60% dispersion of sodium hydride in mineral oil. After stirring for 50 minutes at room temperature, 4.0 g of 2-chloro-4,6-diphenoxy-5-cyanopyrimidine in 25 mL N,N-dimethylformamide was added over 7 minutes. The reaction was heated at 55° C. for 6.5 hours then cooled to room temperature. Water (400 mL) was added and the contents were extracted with dichloromethane. The combined organic layers were dried over sodium sulfate, filtered, and concentrated to a volume of 45 mL. Hexanes (~50 mL) was added and the mixture was filtered, and washed with hexanes (~200 mL) to give 6.05 g of the product as a light yellow solid. The solid was triturated with a minimal amount of dichloromethane then dissolved in dichloromethane (190 mL) and purified by MPLC eluting with 75:25 to 40:60 hexanes:dichloromethane. The purest fractions were combined and concentrated by rotary evaporation to give a solid which was recrystallized twice using equal amounts of THF/hexanes, washing with 1:1 THF:hexanes to give I-4 as gold crystals (1.21 g, 15% yield). Final purification prior to device preparation was accomplished by vacuum sublimation.

Synthesis Example 5

This example illustrates the preparation of Compound I-5.

a. Synthesis of 2,6-Diphenyl-pyrimidin-4-one (Intermediate 5)

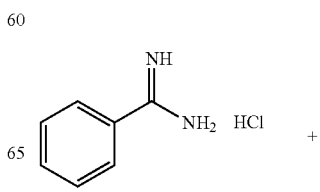

+ c. Synthesis of 2,6-diphenyl-5-cyanopyrimidin-4-one (Intermediate 7)

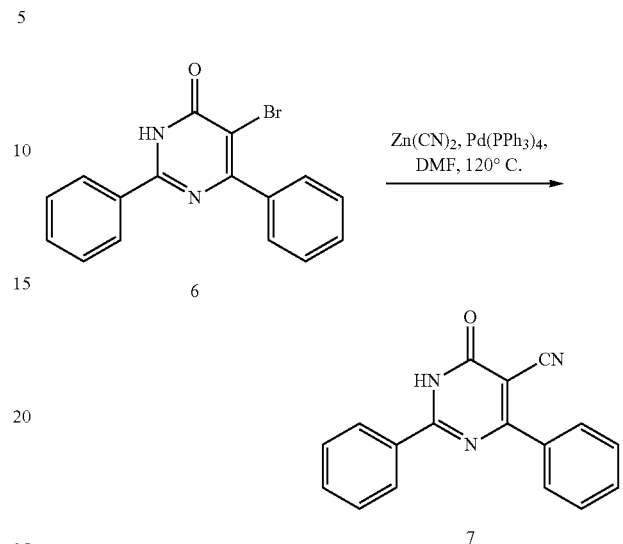

In a glove box, 4.0 g of Intermediate 6 and 4.0 g of Pd(PPh$_3$)$_4$ in 145 mL N,N-dimethylformamide was heated to an internal temperature of 50° C. Next, 2.88 g of zinc cyanide was added and the reaction was heated at an internal temperature of 118° C. overnight. The reaction was cooled, water (1 L) was added to the reaction and the contents were extracted with chloroform. The combined organic layers were dried over sodium sulfate, filtered, and concentrated by rotary evaporation to give a solid which was triturated with dichloromethane to give Intermediate 7 as a white solid (740 mg, 22% yield).

d. Synthesis of 2,6-Diphenyl-5-bromopyrimidin-4-one (Intermediate 8)

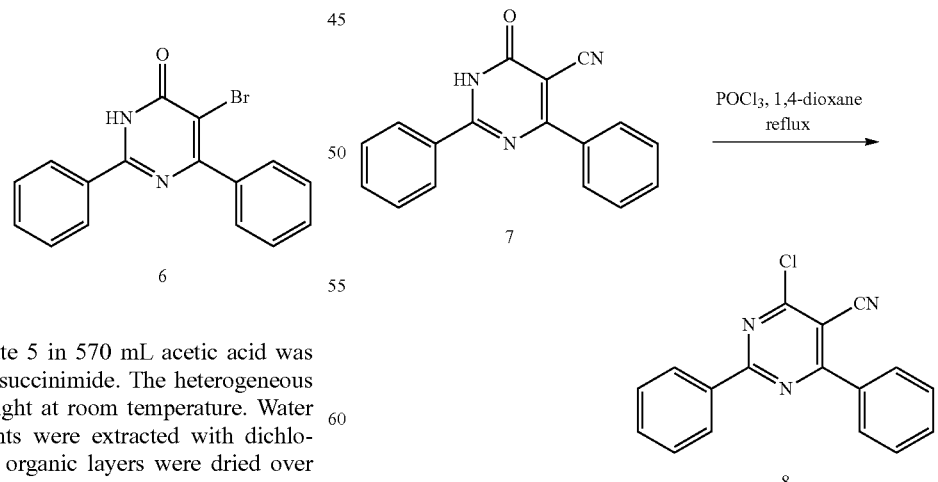

To a suspension of 4.49 g of Intermediate 7 in 76 mL 1,4-dioxane was added 23.5 mL of phosphorus oxychloride. The reaction was refluxed for 3.5 hours, cooled to room

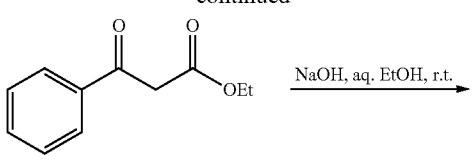

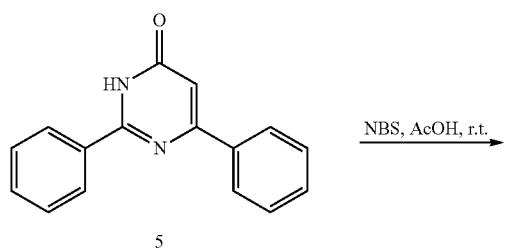

A solution of 18.47 g of benzamidine hydrochloride in 47 mL water was treated with a solution of 4.74 g of sodium hydroxide in 10 mL water. Next, 21.45 mL of ethyl benzoylacetate was added followed by 50 mL ethanol to produce a homogenous reaction, which was stirred overnight at room temp. The heterogeneous reaction was filtered, and the solid was washed with methyl tert-butyl ether to give Intermediate 5 as a white solid. (19.9 g, 68% yield).

b. Synthesis of 2,6-diphenyl-5-bromopyrimidin-4-one (Intermediate 6)

To 19.9 g of Intermediate 5 in 570 mL acetic acid was added 21.4 g of N-bromo-succinimide. The heterogeneous reaction was stirred overnight at room temperature. Water was added and the contents were extracted with dichloromethane. The combined organic layers were dried over sodium sulfate, filtered, and concentrated by rotary evaporation to give a solid which was triturated with hot ethanol and washed twice with ethanol then once with methyl tert-butyl ether to give Intermediate 6 as a white solid (20.25 g, 77% yield).

temperature, and poured into water cooled in an ice bath. As solution of saturated aq. sodium carbonate was added until pH=6, and the contents were extracted with dichloromethane. The combined organic layers were dried over sodium sulfate, filtered, and concentrated by rotary evaporation to provide an off-white solid which was dissolved in dichloromethane and purified by medium pressure liquid chromatography (MPLC) eluting with 70:30 to 50:50 hexanes: dichloromethane. The purest fractions were combined and concentrated by rotary evaporation to give Intermediate 8 as a white solid (3.15 g, 66% yield).

e. Synthesis of 11-(m-terphenyl)-12-(2,6-diphenyl-5-cyanopyrimidin-4-yl)-indolo[2,3-a]carbazole (I-5)

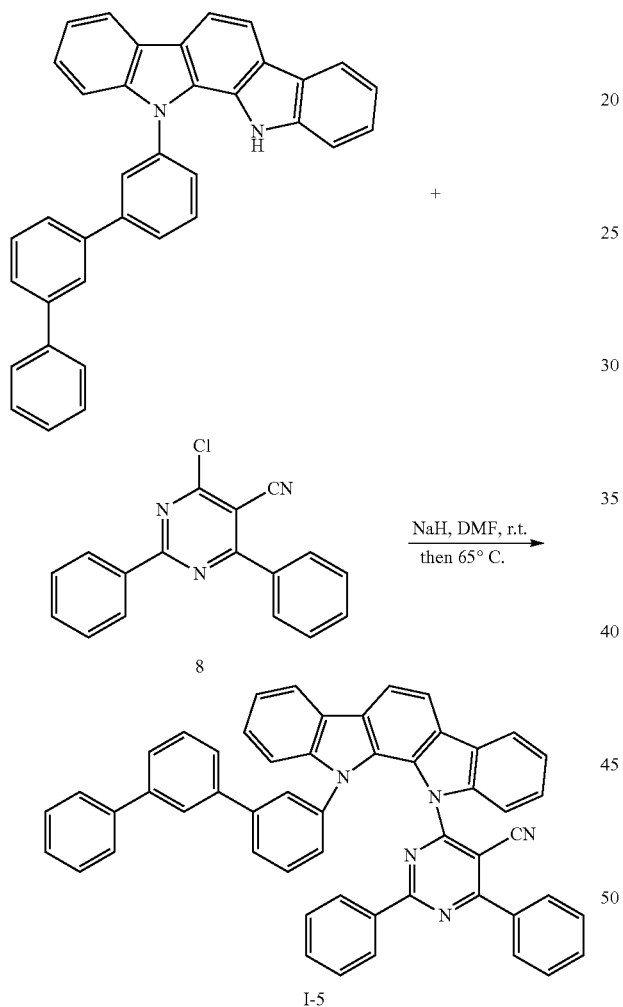

In a glove box, to 4.30 g of 12-[3-(3-phenylphenyl)phenyl]-11H-indolo[2,3-a]carbazole in 31 mL DMF at room temperature was added 434 mg of 60% NaH in 10 mL DMF. After stirring for 1 hour at room temperature, 3.1 g of Intermediate 8 in 103 mL DMF was added. The reaction was heated between 60-65° C. After 3 hours, an additional 55 mg of NaH (60% in mineral oil) in 1 mL DMF was added. After the reaction stirred overnight, water (500 mL) and saturated aqueous ammonium chloride (10 mL) were added. The contents were extracted with dichloromethane, and the combined organic layers were dried over sodium sulfate, filtered,
and concentrated by rotary evaporation to give a gold-orange oil. The crude material was purified by MPLC, eluting with 90:10 to 50:50 hexanes:dichloromethane. The purest fractions were combined and concentrated by rotary evaporation to give a yellow solid which dissolved in dichloromethane, filtered, and carefully concentrated by rotary evaporation from dichloromethane/acetonitrile to give I-5 as a yellow solid (1.32 g, 22% yield, 99.99% purity by UPLC). Final purification prior to device preparation was accomplished by vacuum sublimation.

Device Examples (1) Materials

D1 is a cyclometallated iridium complex. Such materials have been described in, for example, published PCT application WO 2013142634.

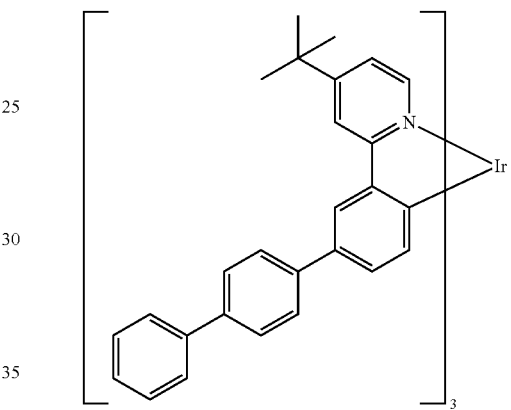

D2 is a cyclometallated iridium complex. Such materials have been described in, for example, U.S. Pat. No. 7,276,716.

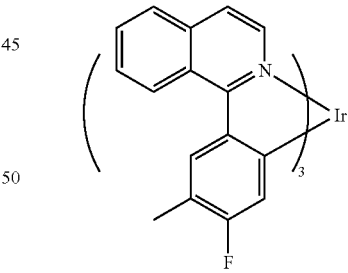

ET-1 is an aryl phosphine oxide.

ET-2 is lithium quinolate.

HIJ-1 is a hole injection material which is made from an aqueous dispersion of an electrically conductive polymer and a polymeric fluorinated sulfonic acid. Such materials have been described in, for example, U.S. Pat. Nos. 7,351,358, 7,431,866, 7,462,298, and published PCT application WO 2009/018009.

Host H1, shown below, is an indolocarbazole. Such materials have been described in, for example, published PCT Application WO 2012087955.

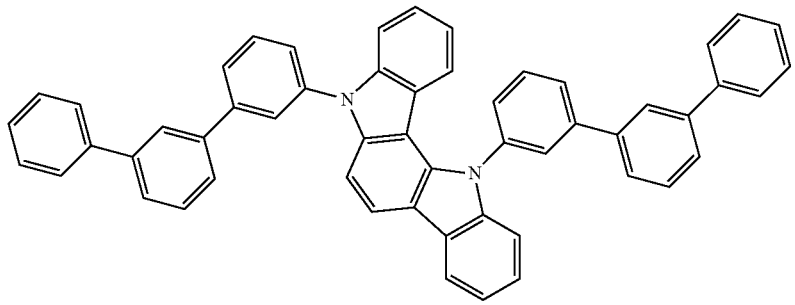 [SMILES: c1ccc(-c2cccc(-c3cccc(-n4c5ccccc5c5c4ccc4c6ccccc6n(-c6cccc(-c7cccc(-c8ccccc8)c7)c6)c45)c3)c2)cc1]

Host H2, shown below, is a deuterated amino-chrysene compound. Such materials have been described in, for example, U.S. Pat. No. 8,968,883.

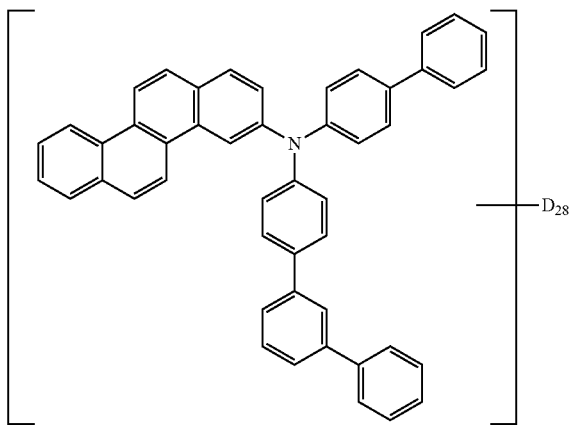

HTM-1 is a triarylamine polymer.

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent to form the hole injection layer ("HIL"). After cooling, the substrates were then spin-coated with a toluene solution of hole transport material, and then heated to remove solvent, to form the hole transport layer ("HTL"). After cooling the substrates were spin-coated with a methyl benzoate solution of the host and dopant, and heated to remove solvent, to form the electroluminescent layer ("EML"). The substrates were masked and placed in a vacuum chamber. A layer of electron transport material was deposited by thermal evaporation to form the electron transport layer ("ETL"). Masks were then changed in vacuo and a layer of Al was deposited by thermal evaporation, to form the cathode. The chamber was vented, and the devices were encapsulated using a glass lid, desiccant, and UV curable epoxy.

(3) Device Characterization

The OLED devices were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The color coordinates were determined using either a Minolta CS-100 meter or a Photoresearch PR-705 meter.

Device Examples 1-4

These examples illustrate the use of a material having Formula I, as the host material in a device. The devices were fabricated as described above, and had the following layers.
Anode=ITO (50 nm)
HIL=HIJ-1 (50 nm)
HTL=HTM-1:HTM-2 (8:2, by weight) (18 nm)
EML=44 wt % first host, 40 wt % second host H1, and 16 wt % D1 (53 nm). The first host is given in Table 1, below.
ETL=ET-1:ET-2 (2:3, by weight) (20 nm)
Cathode=Al (100 nm)
The results are given in Table 1 below.

TABLE 1

| | Device results | | | |
|---|---|---|---|---|
| Ex. | First Host Compound | CE (cd/A) | EQE (%) | T95 (hours) |
| 1 | I-5 | 20 | 7 | 75 |
| 2 | I-2 | 60 | 17 | 75 |
| 3 | I-3 | 72 | 20 | 12 |
| 4 | I-1 | 30 | 8 | 4 |

All data, except T95, at 2000 nits. CE is the current efficiency; EQE=external quantum efficiency; T95 is the time in hours for a device to reach 95% of the initial luminance at 5 mA/cm$^2$ and 50° C.

Device Examples 5-7

These examples illustrate the use of a material having Formula I as the host material in a device. The devices were fabricated as described above, and had the following layers.

Anode=ITO (50 nm)
HIL=HIJ-1 (78 nm)
HTL=HTM-1:HTM-2 (8:2 by weight) (18 nm)
EML=65 wt % first host, 21 wt % second host H2, 8 wt % D2 and 6 wt % D1 (64 nm). The first host is given in Table 2 below.
ETL=ET-1:ET-2 (2:3 by weight) (22 nm)
Cathode=Al (100 nm)
The results are given in Table 2 below.

TABLE 2

Device results

| Ex. | First Host Compound | CE (cd/A) | EQE (%) | T95 (hours) |
|---|---|---|---|---|
| 5 | I-5 | 20.5 | 19.5 | 500 |
| 6 | I-2 | 21.5 | 20.5 | 650 |
| 7 | I-3 | 21 | 20 | 100 |

All data, except T95, at 2000 nits. CE is the current efficiency; EQE=external quantum efficiency; T95 is the time in hours for a device to reach 95% of the initial luminance at 8 mA/cm$^2$ and 50° C.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A compound comprising an N-heterocycle having at least one substituent of Formula I:

wherein:
the N-heterocycle is a fused ring N-heterocycle having at least two fused aromatic rings with at least one ring N;
Q1, Q2, Q4, and Q5 are the same or different and are selected from the group consisting of N and CR$^1$;
Q3 is C—CN;
R$^1$ is the same or different at each occurrence and is selected from the group consisting of H, D, CN, hydrocarbon aryl, heteroaryl, deuterated hydrocarbon aryl, and deuterated heteroaryl; and
* represents a point of attachment to N in the N-heterocycle;
with the proviso that at least one of Q1, Q2, Q4, and Q5 is N.

2. The compound of claim 1, wherein the N-heterocycle is selected from the group consisting of carbazole, benzocarbazole, dibenzocarbazole, indolocarbazole, indole, indoloindole, substituted derivatives thereof, and deuterated analogs thereof.

3. The compound of claim 1, wherein the N-heterocycle is selected from the group consisting of a carbazole having Formula II, a benzocarbazole having Formula II-a, Formula II-b, or Formula II-c, a dibenzocarbazole having Formula II-d, Formula II-e, or Formula II-f, an indole having Formula III-a, and an indoloindole having Formula III-b

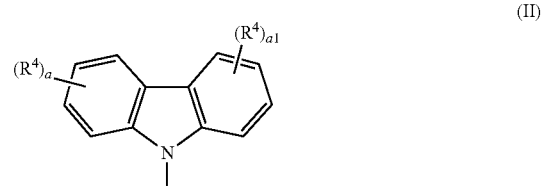

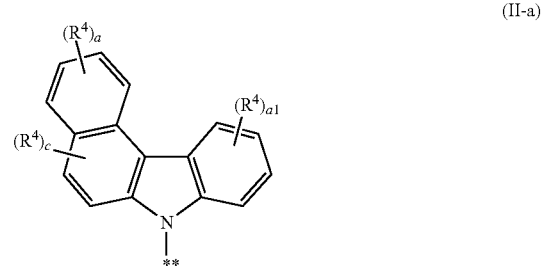

-continued

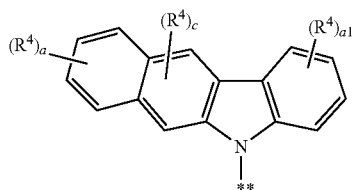
(II-b)

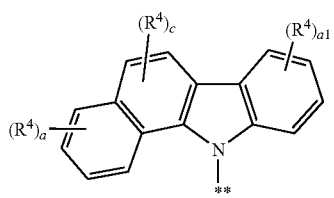
(II-c)

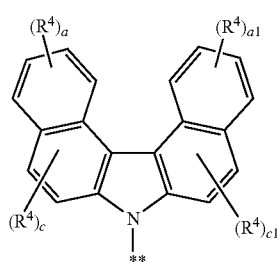
(II-d)

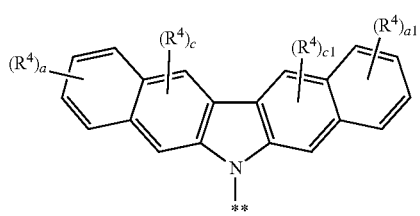
(II-e)

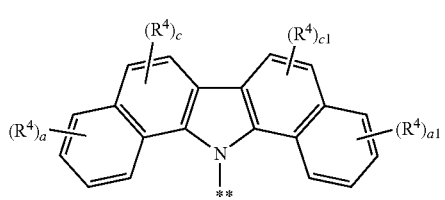
(II-f)

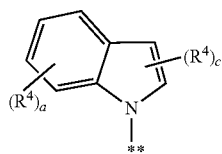
(III-a)

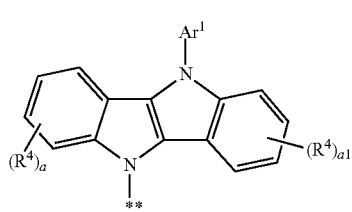
(III-b)

wherein:
Ar¹ is selected from the group consisting of hydrocarbon aryl, heteroaryl, and deuterated analogs thereof;

$R^4$ is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;

a and a1 are the same or different at each occurrence and are an integer from 0 to 4;

c and c1 are the same or different at each occurrence and are an integer from 0-2; and

** represents a point of attachment to the substituent having Formula I;

wherein when a=2, 3, or 4, adjacent $R^4$ groups are unjoined or joined together to form a fused ring;

wherein when a1=2, 3, or 4, adjacent $R^4$ groups are unjoined or joined together to form a fused ring;

wherein when c=2, adjacent $R^4$ groups are unjoined or joined together to form a fused ring.

4. The compound of claim 1, wherein the N-heterocycle is an indolocarbazole having Formula IV-a, Formula IV-b, Formula IV-c, Formula IV-d, or Formula IV-e

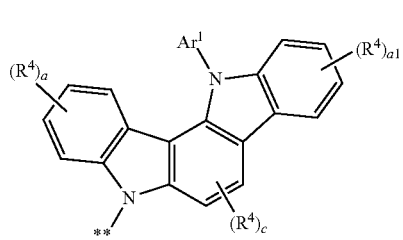
(IV-a)

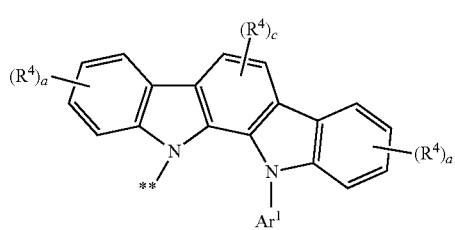
(IV-b)

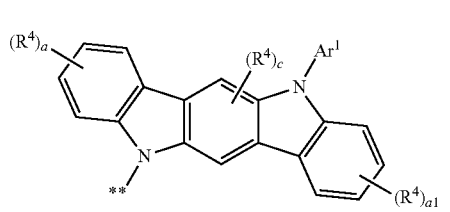
(IV-c)

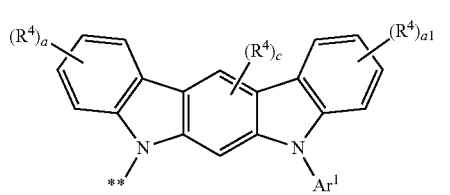
(IV-d)

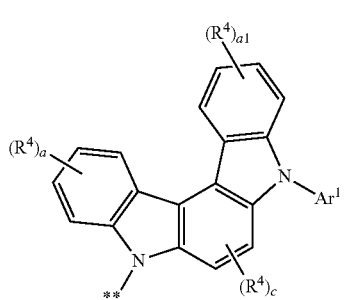

(IV-e)

wherein:
Ar[1] is selected from the group consisting of hydrocarbon aryl, heteroaryl, and deuterated analogs thereof;
R[4] is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;
a and a1 are the same or different and are an integer from 0-4;
c is an integer from 0-2; and
** represents a point of attachment to the substituent having Formula I;
wherein when a=2, 3, or 4, adjacent R[4] groups are unjoined or joined together to form a fused ring;
wherein when a1=2, 3, or 4, adjacent R[4] groups are unjoined or joined together to form a fused ring;
wherein when c=2, adjacent R[4] groups are unjoined or joined together to form a fused ring.

5. The compound of claim 1, wherein at least one of Q1, Q2, Q4, and Q5 is CR[1] where R[1] is H or D.

6. The compound of claim 1, wherein at least one of Q1, Q2, Q4, and Q5 is CR[1] where R[1] is a hydrocarbon aryl or deuterated analog thereof having 6-24 ring carbons.

7. The compound of claim 1, wherein at least one of Q1, Q2, Q4, and Q5 is CR[1] where R[1] is a hydrocarbon aryloxy or deuterated hydrocarbon aryloxy group.

8. The compound of claim 1, wherein the substituent group has Formula IA

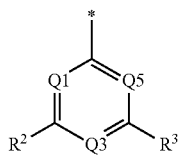

(IA)

wherein:
Q1, and Q5 are the same or different and are selected from the group consisting of N and CR[3];
Q3 is C—CN;
R[1], R[2], and R[3] are the same or different at each occurrence and are selected from the group consisting of H, D, CN, hydrocarbon aryl, heteroaryl, deuterated hydrocarbon aryl, and deuterated heteroaryl; and

* represents a point of attachment to N in the N-heterocycle;
with the proviso that at least one of Q1 and Q5 is N.

9. The compound of claim 1, wherein the substituent has Formula IB

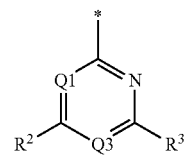

(IB)

wherein:
Q1 is selected from the group consisting of N and CR[3];
Q3 is C—CN;
R[1], R[2], and R[3] are the same or different at each occurrence and are selected from the group consisting of H, D, CN, hydrocarbon aryl, heteroaryl, deuterated hydrocarbon aryl, and deuterated heteroaryl; and
* represents a point of attachment to N in the N-heterocycle.

10. A composition comprising (a) an electroluminescent material having an emission maximum between 380 and 750 nm, (b) a first host compound according to claim 1, and (c) a second host compound.

11. An organic electronic device comprising an anode, a cathode, and at least one organic active layer therebetween, wherein the organic active layer comprises a compound according to claim 1.

12. The device of claim 11, wherein the organic active layer is a photoactive layer.

13. The device of claim 12, wherein the compound according to claim 1 is a first host compound and the photoactive layer further comprises (a) an electroluminescent material having an emission maximum between 380 and 750 nm, and (c) a second host compound.

14. The device of claim 13, wherein the second host compound is selected from the group consisting of indolocarbazoles, chrysenes, substituted derivatives thereof, and deuterated analogs thereof.

15. The device of claim 11, wherein the organic active layer is an electron transport layer.

16. The compound of claim 4, wherein Ar[1] has Formula a

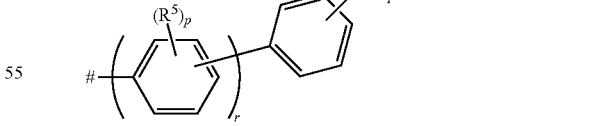

Formula a where:
R[5] is the same or different at each occurrence and is selected from the group consisting of D, alkyl, alkoxy, siloxane, silyl, germyl, diarylamino, carbazolyl, deuterated alkyl, deuterated alkoxy, deuterated siloxane, deuterated silyl, deuterated germyl, deuterated diarylamino, and deuterated carbazolyl, where adjacent R[5] groups can be joined together to form a fused aromatic ring or a deuterated fused aromatic ring;

p is the same or different at each occurrence and is an integer from 0-4;
q is an integer from 0-5;
r is an integer from 1 to 5; and
# indicates a point of attachment.
17. A compound according to claim 1, selected from the group consisting of Compound I-1 through Compound I-4
Compound I-1
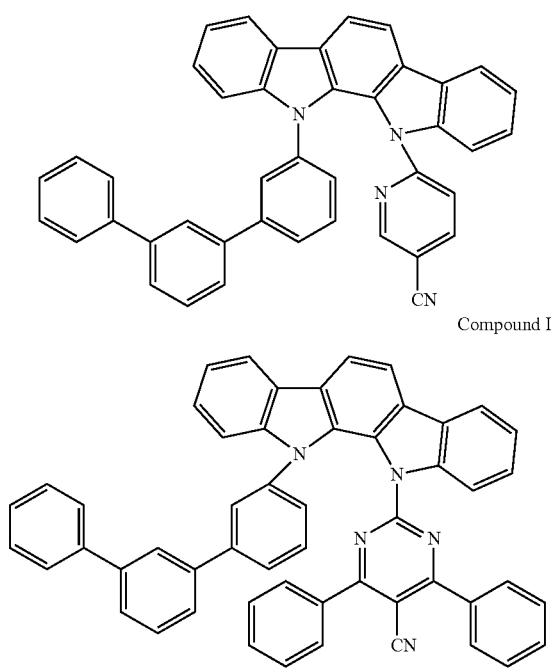
Compound I-2
Compound I-3
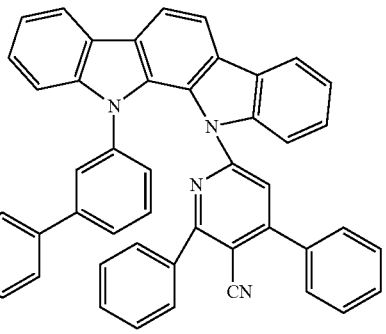
Compound I-4
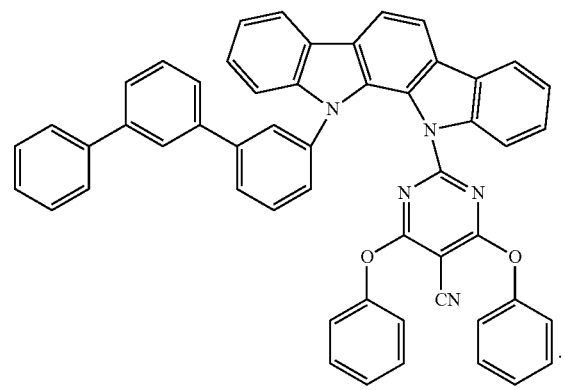
* * * * *